United States Patent
Ledbetter et al.

(10) Patent No.: US 11,604,237 B2
(45) Date of Patent: Mar. 14, 2023

(54) DEVICES, SYSTEMS, AND METHODS WITH OPTICAL PUMPING MAGNETOMETERS FOR THREE-AXIS MAGNETIC FIELD SENSING

(71) Applicant: HI LLC, Los Angeles, CA (US)

(72) Inventors: Micah Ledbetter, Sunnyvale, CA (US); Benjamin Shapiro, Culver City, CA (US); Ethan Pratt, Santa Clara, CA (US); Ricardo Jimenez-Martinez, Culver City, CA (US); Argyrios Dellis, Plymouth, MN (US); Kayla Wright-Freeman, Pasadena, CA (US); Geoffrey Iwata, San Francisco, CA (US); Michael Romalis, Princeton, NJ (US)

(73) Assignee: HI LLC, Los Angeles, CA (US)

( * ) Notice: Subject to any disclaimer, the term of this patent is extended or adjusted under 35 U.S.C. 154(b) by 0 days.

(21) Appl. No.: 17/569,287

(22) Filed: Jan. 5, 2022

(65) Prior Publication Data
US 2022/0397618 A1 Dec. 15, 2022

Related U.S. Application Data

(60) Provisional application No. 63/158,700, filed on Mar. 9, 2021, provisional application No. 63/135,364, filed on Jan. 8, 2021.

(51) Int. Cl.
*G01R 33/26* (2006.01)
(52) U.S. Cl.
CPC .................................. *G01R 33/26* (2013.01)
(58) Field of Classification Search
CPC .................................................... G01R 33/26
See application file for complete search history.

(56) References Cited

U.S. PATENT DOCUMENTS

| 3,173,082 A | 3/1965 | Bell et al. |
| 3,257,608 A | 6/1966 | Bell et al. |

(Continued)

FOREIGN PATENT DOCUMENTS

| CN | 104730484 | 6/2015 |
| CN | 107562188 | 1/2018 |

(Continued)

OTHER PUBLICATIONS

Allred, J. C., Lyman, R. N., Kornack, T. W., & Romalis, M. V. (2002). High-sensitivity atomic magnetometer unaffected by spin-exchange relaxation. Physical review letters, 89(13), 130801.

(Continued)

*Primary Examiner* — Jay Patidar
(74) *Attorney, Agent, or Firm* — Branch Partners PLLC; Bruce E. Black

(57) ABSTRACT

A magnetic field measurement system includes a magnetometer having at least one vapor cell, at least one light source to direct at least two light beams through the vapor cell(s), and at least one detector; at least one magnetic field generator to modify an external magnetic field experienced by the vapor cell(s); and at least one processor configured for: applying a first modulation pattern, $b_{mod}(t)$, to the magnetic field generator(s) to modulate a magnetic field at the vapor cell(s), where $b_{mod}(t)=[c_x \cos(\omega t)+s_x \sin(\omega t), c_y \cos(\omega t)+s_y \sin(\omega t), c_z \cos(\omega t)+s_z \sin(\omega t)]$, where $c_x, s_x, c_y, s_y, c_z$, and $s_z$ are amplitudes and $\omega$ is a frequency; directing the light source(s) to direct the light beams through the vapor cell(s); receiving signals from the detector(s); and determining three orthogonal components of the external magnetic field using the received signals. Multi-frequency modulation patterns can alternatively be used.

20 Claims, 5 Drawing Sheets

(56) References Cited

U.S. PATENT DOCUMENTS

| | | |
|---|---|---|
| 3,495,161 A | 2/1970 | Bell |
| 3,501,689 A | 3/1970 | Robbiano |
| 3,513,381 A | 5/1970 | Happer, Jr. |
| 4,193,029 A | 3/1980 | Cioccio et al. |
| 4,951,674 A | 8/1990 | Zanakis et al. |
| 5,189,368 A | 2/1993 | Chase |
| 5,192,921 A | 3/1993 | Chantry et al. |
| 5,225,778 A | 7/1993 | Chaillout et al. |
| 5,254,947 A | 10/1993 | Chaillout et al. |
| 5,309,095 A | 5/1994 | Ahonen et al. |
| 5,442,289 A | 8/1995 | Dilorio et al. |
| 5,444,372 A | 8/1995 | Wikswo, Jr. et al. |
| 5,471,985 A | 12/1995 | Warden |
| 5,506,200 A | 4/1996 | Hirschkoff et al. |
| 5,526,811 A | 6/1996 | Lypchuk |
| 5,713,354 A | 2/1998 | Warden |
| 6,144,872 A | 11/2000 | Graetz |
| 6,339,328 B1 | 1/2002 | Keene et al. |
| 6,472,869 B1 | 10/2002 | Upschulte et al. |
| 6,665,553 B2 | 12/2003 | Kandor et al. |
| 6,806,784 B2 | 10/2004 | Hollberg et al. |
| 6,831,522 B2 | 12/2004 | Kitching et al. |
| 7,038,450 B2 | 5/2006 | Romalis et al. |
| 7,102,451 B2 | 9/2006 | Happer et al. |
| 7,145,333 B2 | 12/2006 | Romalis et al. |
| 7,521,928 B2 | 4/2009 | Romalis et al. |
| 7,656,154 B2 | 2/2010 | Kawabata et al. |
| 7,826,065 B1 | 11/2010 | Okandan et al. |
| 7,872,473 B2 | 1/2011 | Kitching et al. |
| 7,994,783 B2 | 8/2011 | Ledbetter et al. |
| 8,054,074 B2 | 11/2011 | Ichihara et al. |
| 8,212,556 B1 | 7/2012 | Schwindt et al. |
| 8,258,884 B2 | 9/2012 | Borwick, III et al. |
| 8,319,156 B2 | 11/2012 | Borwick, III et al. |
| 8,334,690 B2 | 12/2012 | Kitching et al. |
| 8,373,413 B2 | 2/2013 | Sugioka |
| 8,405,389 B2 | 3/2013 | Sugioka et al. |
| 8,587,304 B2 | 11/2013 | Budker et al. |
| 8,836,327 B2 | 9/2014 | French et al. |
| 8,906,470 B2 | 12/2014 | Overstolz et al. |
| 8,941,377 B2 | 1/2015 | Mizutani et al. |
| 9,084,549 B2 | 7/2015 | Desain et al. |
| 9,095,266 B1 | 8/2015 | Fu |
| 9,116,201 B2 | 8/2015 | Shah et al. |
| 9,140,590 B2 | 9/2015 | Waters et al. |
| 9,140,657 B2 | 9/2015 | Ledbetter et al. |
| 9,169,974 B2 | 10/2015 | Parsa et al. |
| 9,244,137 B2 | 1/2016 | Kobayashi et al. |
| 9,291,508 B1 | 3/2016 | Biedermann et al. |
| 9,343,447 B2 | 3/2016 | Parsa et al. |
| 9,366,735 B2 | 6/2016 | Kawabata et al. |
| 9,383,419 B2 | 7/2016 | Mizutani et al. |
| 9,395,425 B2 | 7/2016 | Diamond et al. |
| 9,417,293 B2 | 8/2016 | Schaffer et al. |
| 9,429,918 B2 | 8/2016 | Parsa et al. |
| 9,568,565 B2 | 2/2017 | Parsa et al. |
| 9,575,144 B2 | 2/2017 | Kornack et al. |
| 9,601,225 B2 | 3/2017 | Parsa et al. |
| 9,638,768 B2 | 5/2017 | Foley et al. |
| 9,639,062 B2 | 5/2017 | Dyer et al. |
| 9,677,905 B2 | 6/2017 | Waters et al. |
| 9,726,626 B2 | 8/2017 | Smith et al. |
| 9,726,733 B2 | 8/2017 | Smith et al. |
| 9,791,536 B1 | 10/2017 | Alem et al. |
| 9,829,544 B2 | 11/2017 | Bulatowicz |
| 9,846,054 B2 | 12/2017 | Waters et al. |
| 9,851,418 B2 | 12/2017 | Wolf et al. |
| 9,869,731 B1 | 1/2018 | Hovde et al. |
| 9,915,711 B2 | 3/2018 | Kornack et al. |
| 9,927,501 B2 | 3/2018 | Kim et al. |
| 9,948,314 B2 | 4/2018 | Dyer et al. |
| 9,964,609 B2 | 5/2018 | Ichihara et al. |
| 9,964,610 B2 | 5/2018 | Shah et al. |
| 9,970,999 B2 | 5/2018 | Larsen et al. |
| 9,995,800 B1 | 6/2018 | Schwindt et al. |
| 10,024,929 B2 | 7/2018 | Parsa et al. |
| 10,088,535 B1 | 10/2018 | Shah |
| 10,162,016 B2 | 12/2018 | Gabrys et al. |
| 10,194,865 B2 | 2/2019 | Le et al. |
| 10,314,508 B2 | 6/2019 | Desain et al. |
| 10,371,764 B2 | 8/2019 | Morales et al. |
| 10,772,561 B2 | 9/2020 | Donaldson |
| 2004/0232912 A1 | 11/2004 | Tsukamoto et al. |
| 2005/0007118 A1 | 1/2005 | Kitching et al. |
| 2005/0046851 A1 | 3/2005 | Riley, Jr. et al. |
| 2005/0206377 A1 | 9/2005 | Romalis et al. |
| 2007/0120563 A1 | 5/2007 | Kawabata et al. |
| 2007/0167723 A1 | 7/2007 | Park et al. |
| 2007/0205767 A1 | 9/2007 | Xu et al. |
| 2009/0079426 A1 | 3/2009 | Anderson |
| 2009/0101806 A1 | 4/2009 | Masuda |
| 2010/0219820 A1 | 9/2010 | Skidmore et al. |
| 2011/0062956 A1 | 3/2011 | Edelstein et al. |
| 2012/0112749 A1 | 5/2012 | Budker et al. |
| 2013/0082700 A1 | 4/2013 | Mizutani et al. |
| 2013/0082701 A1 | 4/2013 | Mizutani et al. |
| 2013/0265042 A1 | 10/2013 | Kawabata et al. |
| 2014/0121491 A1 | 5/2014 | Zhang |
| 2014/0306700 A1 | 10/2014 | Kamada et al. |
| 2014/0354275 A1 | 12/2014 | Sheng et al. |
| 2015/0022200 A1 | 1/2015 | Ichihara et al. |
| 2015/0054504 A1 | 2/2015 | Ichihara et al. |
| 2015/0378316 A1 | 12/2015 | Parsa et al. |
| 2016/0061913 A1 | 3/2016 | Kobayashi et al. |
| 2016/0116553 A1 | 4/2016 | Kim et al. |
| 2016/0223627 A1 | 8/2016 | Shah et al. |
| 2016/0291099 A1 | 10/2016 | Ueno |
| 2016/0313417 A1 | 10/2016 | Kawabata et al. |
| 2017/0023653 A1 | 1/2017 | Kobayashi et al. |
| 2017/0023654 A1 | 1/2017 | Kobayashi et al. |
| 2017/0067969 A1 | 3/2017 | Butters et al. |
| 2017/0199138 A1 | 7/2017 | Parsa et al. |
| 2017/0261564 A1 | 9/2017 | Gabrys et al. |
| 2017/0331485 A1 | 11/2017 | Gobet et al. |
| 2017/0343617 A1 | 11/2017 | Manickam et al. |
| 2017/0343695 A1 | 11/2017 | Stetson et al. |
| 2017/0356969 A1 | 12/2017 | Ueno |
| 2017/0360322 A1 | 12/2017 | Ueno |
| 2017/0363695 A1 | 12/2017 | Ueno |
| 2018/0003777 A1 | 1/2018 | Sorenson et al. |
| 2018/0038921 A1 | 2/2018 | Parsa et al. |
| 2018/0100749 A1 | 4/2018 | Waters et al. |
| 2018/0128885 A1 | 5/2018 | Parsa et al. |
| 2018/0156875 A1 | 6/2018 | Herbsommer et al. |
| 2018/0219353 A1 | 8/2018 | Shah |
| 2018/0238974 A1 | 8/2018 | Shah et al. |
| 2018/0313908 A1 | 11/2018 | Knappe et al. |
| 2018/0313913 A1 | 11/2018 | DeNatale et al. |
| 2018/0372813 A1 | 12/2018 | Bulatowicz et al. |
| 2019/0391213 A1 | 12/2019 | Alford |
| 2020/0025844 A1 | 1/2020 | Alford et al. |
| 2020/0056263 A1 | 2/2020 | Bhattacharyya et al. |
| 2020/0057115 A1 | 2/2020 | Jimenez-Martinez et al. |
| 2020/0057116 A1 | 2/2020 | Zorzos et al. |
| 2020/0064421 A1 | 2/2020 | Kobayashi et al. |
| 2020/0072916 A1 | 3/2020 | Alford et al. |
| 2020/0088811 A1 | 3/2020 | Mohseni |
| 2020/0109481 A1 | 4/2020 | Sobek et al. |
| 2020/0123416 A1 | 4/2020 | Bhattacharyya et al. |
| 2020/0191883 A1 | 6/2020 | Bhattacharyya et al. |
| 2020/0241094 A1 | 7/2020 | Alford |
| 2020/0256929 A1 | 8/2020 | Ledbetter et al. |
| 2020/0309873 A1 | 10/2020 | Ledbetter et al. |
| 2020/0334559 A1 | 10/2020 | Anderson et al. |
| 2020/0341081 A1 | 10/2020 | Mohseni et al. |
| 2020/0381128 A1 | 12/2020 | Pratt et al. |
| 2020/0400763 A1 | 12/2020 | Pratt |
| 2021/0011094 A1 | 1/2021 | Bednarke |
| 2021/0015385 A1 | 1/2021 | Katnani et al. |
| 2021/0015427 A1 | 1/2021 | Shah et al. |
| 2021/0041512 A1 | 2/2021 | Pratt et al. |

(56) References Cited

U.S. PATENT DOCUMENTS

2021/0041513 A1 2/2021 Mohseni
2021/0063510 A1 3/2021 Ledbetter

FOREIGN PATENT DOCUMENTS

| CN | 110742607 | 2/2020 |
|---|---|---|
| CN | 110859610 | 3/2020 |
| EP | 2738627 A3 | 6/2014 |
| EP | 2380029 B1 | 10/2015 |
| EP | 3037836 B1 | 9/2017 |
| JP | 2016109665 | 6/2016 |
| JP | 2018004462 | 1/2018 |
| WO | 92/01362 | 1/1992 |
| WO | 2005/081794 | 9/2005 |
| WO | 2014/031985 | 2/2014 |
| WO | 2017/095998 | 6/2017 |
| WO | 2020/084194 | 4/2020 |

OTHER PUBLICATIONS

Balabas et al. Polarized alkali vapor with minute-long transverse spin-relaxation time, Phys. Rev. Lett 105, 070801—Published Aug. 12, 2010.

Barbieri, F., Trauchessec, V., Caruso, L., Trejo-Rosillo, J., Telenczuk, B., Paul, E., . . . & Ouanounou, G. (2016). Local recording of biological magnetic fields using Giant Magneto Resistance-based micro-probes. Scientific reports, 6, 39330.

Dmitry Budker and Michael Romalis, "Optical Magnetometry," Nature Physics, 2008, https://arxiv.org/abs/physics/0611246v1.

Anthony P. Colombo, Tony R. Carter, Amir Boma, Yuan-Yu Jau, Cort N. Johnson, Amber L. Dagel, and Peter D. D. Schwindt, "Four-channel optically pumped atomic magnetometer for magnetoencephalography," Opt. Express 24, 15403-15416 (2016).

Dang, H.B. & Maloof, A.C. & Romalis, Michael. (2009). Ultra-high sensitivity magnetic field and magnetization measurements with an atomic magnetometer. Applied Physics Letters. 97. 10.1063/1.3491215.

Donley, E.A. & Hodby, E & Hollberg, L & Kitching, J. (2007). Demonstration of high-performance compact magnetic shields for chip-scale atomic devices. The Review of scientific instruments. 78. 083102.

Hämäläinen, Matti & Hari, Riitta & Ilmoniemi, Risto J. & Knuutila, Jukka & Lounasmaa, Olli V. Apr. 1993. Magnetoencephalograph—theory, instrumentation, and applications to noninvasive studies of the working human brain. Reviews of Modern Physics. vol. 65, Issue 2. 413-497.

Hunter, D. and Piccolomo, S. and Pritchard, J. D. and Brockie, N. L. and Dyer, T. E. and Riis, E. (2018) Free-induction-decay magnetometer based on a microfabricated Cs vapor cell Physical Review Applied (10).ISSN 2331-7019.

Jiménez-Martínez, R., Griffith, W. C., Wang, Y. J., Knappe, S., Kitching, J., Smith, K., & Prouty, M. D. (2010). Sensitivity comparison of Mx and frequency-modulated bell-bloom Cs magnetometers in a microfabricated cell. IEEE Transactions on Instrumentation and Measurement, 59(2), 372-378.

Kiwoong Kim, Sarno Begus, Hui Xia, Seung-Kyun Lee, Vojko Jazbinsek, Zvonko Trontelj, Michael V. Romalis, Multi-channel atomic magnetometer for magnetoencephalography: A configuration study. NeuroImage 89 (2014) 143-151 http://physics.princeton.edu/romalis/papers/Kim_2014.pdf.

Knappe, Svenja & Sander, Tilmann & Trahms, Lutz. (2012). Optically-Pumped Magnetometers for MEG. Magnetoencephalography: From Signals to Dynamic Cortical Networks. 993-999. 10.1007/978-3-642-33045-2_49.

Kominis, I.K., Kornack, T.W., Allred, J.C. and Romalis, M.V., 2003. A subfemtotesla multichannel atomic magnetometer. Nature, 422(6932), p. 596.

Korth, H., K. Strohbehn, F. Tejada, A. G. Andreou, J. Kitching, S. Knappe, S. J. Lehtonen, S. M. London, and M. Kafel (2016), Miniature atomic scalarmagnetometer for space based on the rubidium isotope 87Rb, J. Geophys. Res. Space Physics, 121, 7870-7880, doi: 10.1002/2016JA022389.

Lenz, J. and Edelstein, S., 2006. Magnetic sensors and their applications. IEEE Sensors journal, 6(3), pp. 631-649.

Li, S & Vachaspati, Pranjal & Sheng, Dehong & Dural, Nezih & Romalis, Michael. (2011). Optical rotation in excess of 100 rad generated by Rb vapor in a multipass cell. Phys. Rev. A. 84.10. 1103/PhysRevA.84.061403.

Maze, J. R., Stanwix, P. L., Hodges, J. S., Hong, S., Taylor, J. M., Cappellaro, P., . . . & Yacoby, A. (2008). Nanoscale magnetic sensing with an individual electronic spin in diamond. Nature, 455(7213), 644.

Sander TH, Preusser J, Mhaskar R, Kitching J, Trahms L, Knappe S. Magnetoencephalography with a chip-scale atomic magnetometer. Biomed Opt Express. 2012;3(5):981-90.

J. Seltzer, S & Romalis, Michael. (2010). High-temperature alkali vapor cells with antirelaxation surface coatings. Journal of Applied Physics. 106. 114905-114905. 10.1063/1.3236649.

Seltzer, S. J., and Romalis, M.V., "Unshielded three-axis vector operation of a spin-exchange-relaxation-free atomic magnetometer." Applied physics letters 85.20 (2004): 4804-4806.

Sheng, Dong & R. Perry, Abigail & Krzyzewski, Sean & Geller, Shawn & Kitching, John & Knappe, Svenja. (2017). A microfabricated optically-pumped magnetic gradiometer. Applied Physics Letters 110. 10.1063/1.4974349.

Sheng, Dehong & Li, S & Dural, Nezih & Romalis, Michael. (2013). Subfemtotesla Scalar Atomic Magnetometry Using Multipass Cells. Physical review letters. 110. 160802. 10.1103/PhysRevLett.110.160802.

Volkmar Schultze et al. An Optically Pumped Magnetometer Working in the Light-Shift Dispersed Mz Mode, Sensors 2017, 17, 561; doi:10.3390/s17030561.

Fang, J. and Qin, J., 2012. In situ triaxial magnetic field compensation for the spin-exchange-relaxation-free atomic magnetometer. Review of Scientific Instruments, 83(10), p. 103104.

Joon Lee, Hyun & Shim, Jeong & Moon, Han Seb & Kim, Kiwoong. (2014). Flat-response spin-exchange relaxation free atomic magnetometer under negative feedback Optics Express. 22. 10.1364/OE.22.019887.

Griffilh, Clark & Jimenez-Martinez, Ricardo & Shah, Vishal & Knappe, Svenja & Kitching, John. (2009). Miniature atomic magnetometer integrated with flux concentrators. Applied Physics Letters—Appl Phys Lett. 94. 10.1063/1.3056152.

Lee, S.-K & Romalis, Michael. (2008). Calculation of Magnetic Field Noise from High-Permeability Magnetic Shields and Conducting Objects with Simple Geometry. Journal of Applied Physics. 103. 084904-084904. 10.1063/1.2885711.

Vovrosh, Jamie & Voulazeris, Georgios & Petrov, Plamen & Zou, Ji & Gaber Beshay, Youssef & Benn, Laura & Woolger, David & Attallah, Moataz & Boyer, Vincent & Bongs, Kai & Holynski, Michael. (2018). Additive manufacturing of magnetic shielding and ultra-high vacuum flange for cold atom sensors. Scientific Reports. 8. 10.1038/s41598-018-20352-x.

Kim, Young Jin & Savukov, I. (2016). Ultra-sensitive Magnetic Microscopy with an Optically Pumped Magnetometer. Scientific Reports 6. 24773. 10.1038/srep24773.

Navau, Carles & Prat-Camps, Jordi & Sanchez, Alvaro. (2012). Magnetic Energy Harvesting and Concentration at a Distance by Transformation Optics. Physical review letters. 109. 263903. 10.1103/PhysRevLett.109.263903.

Orang Alem, Rahul Mhaskar, Ricardo Jimenez-Martinez, Dong Sheng, John LeBlanc, Lutz Trahms, Tilmann Sander, John Kitching, and Svenja Knappe, "Magnetic field imaging with microfabricated optically-pumped magnetometers," Opt. Express 25, 7849-7858 (2017).

Slocum et al., Self-Calibrating Vector Magnetometer for Space, https://esto.nasa.gov/conferences/estc-2002/Papers/B3P4(Slocum).pdf.

(56) References Cited

OTHER PUBLICATIONS

Dupont-Roc, J & Haroche, S & Cohen-Tannoudji, C. (1969). Detection of very weak magnetic fields (10-9gauss) by 87Rb zero-field level crossing resonances. Physics Letters A—Phys Lett A. 28. 638-639.10.1016/0375-9601(69) 90480-0.

J. A. Neuman, P. Wang, and A. Gallagher, Robust high-temperature sapphire cell for metal vapors, Review of Scientific Instruments, vol. 66, Issue 4, Apr. 1995, pp. 3021-3023.

Borna, Amir, et al. "A 20-channel magnetoencephalography system based on optically pumped magnetometers." Physics in Medicine & Biology 62.23 (2017): 8909.

R. E. Slocum & L. J. Ryan, Design and operation of the minature vector laser magnetometer, Nasa Earth Science Technology Conference 2003.

Schoenmaker, Jeroen & R Pirota, K & Teixeira, Julio. (2013). Magnetic flux amplification by Lenz lenses. The Review of scientific instruments. 84. 085120. 10.1063/1.4819234.

Hu, Yanhui & Hu, Zhaohui & Liu, Xuejing & Li, Yang & Zhang, Ji & Yao, Han & Ding, Ming. (2017). Reduction of far off-resonance laser frequency drifts based on the second harmonic of electro-optic modulator detection in the optically bumped magnetometer. Applied Optics. 56. 5927. 10.1364/AO.56.005927.

Masuda, Y & Ino, T & Skoy, Vadim & Jones, G.L. (2005). 3He polarization via optical pumping in a birefringent cell. Applied Physics Letters. 87. 10.1063/1.2008370.

A.B. Baranga et al., An atomic magnetometer for brain activity imaging, Real Time Conference 2005. 14th IEEE-NPSS pp. 417-418.

Larry J. Ryan, Robert E. Slocum, and Robert B. Steves, Miniature Vector Laser Magnetometer Measurements of Earth's Field, May 10, 2004, 4 pgs.

Lorenz, V. O., Dai, X., Green, H., Asnicar, T. R., & Cundiff, S. T. (2008). High-density, high-temperature alkali vapor cell. Review of Scientific Instruments, 79(12), 4 pages.

F. Jackson Kimball, D & Dudley, J & Li, Y & Thulasi, Swecha & Pustelny, Szymon & Budker, Dmitry & Zolotorev, Max. (2016). Magnetic shielding and exotic spin-dependent interactions. Physical Review D. 94. 10.1103/PhysRevD.94.082005.

Huang, Haichao, et al. "Single-beam three-axis atomic magnetometer." Applied Physics Letters 109.6 (2016): 062404. (Year: 2016).

Scott Jeffrey Seltzer: "Developments in alkali-metal atomic magnetometry", Nov. 1, 2008 (Nov. 1, 2008), XP055616618, ISBN: 978-0-549-93355-7 Retrieved from the Internet: URL:http://physics.princeton.edu/atomic/romalis/papers/Seltzer%20Thesis.pdf [retrieved on Aug. 29, 2019] pp. 148-159.

Haifeng Dong et al: "Atomic-Signal-Based Zero-Field Finding Technique for Unshielded Atomic Vector Magnetometer", IEEE Sensors Journal, IEEE Service Center, New York, NY, US, vol. 13, No. 1, Jan. 1, 2013 (Jan. 1, 2013), pp. 186-189.

Boto, E, Holmes, N, Leggett, J, Roberts, G, Shah, V, Meyer, SS, Munoz, LD, Mullinger, KJ, Tierney, TM, Bestmann, S, Barnes, GR, Bowtell, R & Brookes, MJ 2018, 'Moving magnetoencephalography towards real world applications with a wearable system', Nature, vol. 555, pp. 657-661.

Ijsselsteijn, R & Kielpinski, Mark & Woetzel, S & Scholtes, Theo & Kessler, Ernst & Stolz, Ronny & Schultze, V & Meyer, H-G. (2012). A full optically operated magnetometer array: An experimental study. The Review of scientific instruments. 83. 113106. 10.1063/1.4766961.

Tierney, T. M., Holmes, N., Meyer, S. S., Boto, E., Roberts, G., Leggett, J., . . . Barnes, G. R. (2018). Cognitive neuroscience using wearable magnetometer arrays: Non-invasive assessment of language function. NeuroImage, 181, 513-520.

Manon Kok, Jeroen D. Hol and Thomas B. Schon (2017), "Using Inertial Sensors for Position and Orientation Estimation", Foundations and Trends in Signal Processing: vol. 11: No. 1-2, pp. 1-153. http://dx.doi.org/10.1561/2000000094.

Okada, Y.C., Lahteenmäki, A. and Xu, C., "Experimental analysis of distortion of magnetoencephalography signals by the skull." Clinical neurophysiology 110 (2), 230-238 (1999).

Robinson, J.T., Pohlmeyer, E., Gather, M.C., Kemere, C., Kitching, J.E., Malliaras, G.G., Marblestone, A., Shepard, K.L., Stieglitz, T. and Xie, C., "Developing Next-Generation Brain Sensing Technologies—A Review." IEEE sensors journal, 19(22), 10163-10175(2019).

Shah, V., Knappe, S., Schwindt, P.D. and Kitching, J., "Subpicotesla atomic magnetometry with a microfabricated vapour cell." Nature Photon 1, 649-652 (2007).

Giillith, W.C., Knappe, S. and Kitching, J., "Femtotesla atomic magnetometry in a microfabricated vapor cell." Optics express 18, (26), 27167-27172 (2010).

Tierney, T.M., Holmes, N., Mellor, S., López, J.D., Roberts, G., Hill, R.M., Boto, E., Leggett, J., Shah, V., Brookes, M.J. and Bowtell, R., "Optically pumped magnetometers: From quantum origins to multi-channel magnetoencephalography." NeuroImage, 199, 598-608 (2019).

Iivanainen, J., Zetter, R., Grön, M., Hakkarainen, K. and Parkkonen, L., "On-scalp MEG system utilizing an actively shielded array of optically-pumped magnetometers." Neuroimage 194, 244-258 (2019).

Ivanainen, J., Stenroos, M. and Parkkonen, L., "Measuring MEG closer to the brain: Performance of on-scalp sensor arrays." NeuroImage 147, 542-553 (2017).

Kitching, J., Knappe, S., Gerginov, V., Shah, V., Schwindt, P.D., Lindseth, B., Donley E.A., "Chip-scale atomic devices: precision atomic instruments based on MEMS." In Frequency Standards and Metrology, 445-453 (2009).

Kitching, J., Knappe, S. and Donley, E.A., "Atomic sensors—a review." IEEE Sensors Journal, 11(9), 1749-1758 (2011).

Budker, D. and Romalis, M., "Optical magnetometry". Nature physics, 3(4), 227-234 (2007).

Happer, W., "Optical pumping", Rev. Mod. Phys., 44 (2), 169-249 (1972).

Purcell, E.M., Field, G.B., "Influence of collisions upon population of hyperfine states in hydrogen", Astrophys. J., 124, 542 (1956).

Ledbetter, M.P., Savukov, I.M., Acosta, V.M., Budker, D. and Romalis, M.V., "Spin-exchange-relaxation-free magnetometry with Cs vapor." Physical Review A, 77(3), 033408 (2008).

Bloom, A. L., "Principles of operation of the rubidium vapor magnetometer." Applied Optics 1(1), 61-68 (1962).

Bell, W.E., and Bloom, A.L., "Optically driven spin precession." Physical Review Letters 6, (6), 280 (1961).

Roberts, G., Holmes, N., Alexander, N., Boto, E., Leggett, J., Hill, R.M., Shah, V., Rea, M., Vaughan, R., Maguire, E.A. and Kessler, K., "Towards OPM-MEG in a virtual reality environment" NeuroImage, 199, 408-417 (2019).

Zhang, R., Xiao, W., Ding, Y., Feng, Y., Peng, X., Shen, L., Sun, C., Wu, T., Wu, Y., Yang, Y. and Zheng, Z., "Recording brain activities in unshielded Earth's field with optically pumped atomic magnetometers." Science Advances, 6(24) (2020).

De Cheveigné, A., Wong, D.D., Di Liberto, G.M., Hjortkjaer, J., Slaney, M. and Lalor, E., "Decoding the auditory brain with canonical component analysis." NeuroImage, 172, 206-216 (2018).

Mellinger, J., Schalk, G., Braun, C., Preissl, H., Rosenstiel, W., Birbaumer, N. and Kubler, A., "An MEG-based brain-computer interface (BCI) " Neuroimage, 36(3), 581-593 (2007).

Wolpaw, J.R., McFarland, D.J., Neat, G.W. and Forneris, C.A., "An EEG-based brain-computer interface for cursor control." Electroencephalography and clinical neurophysiology, 78(3), 252-259 (1991).

Lightfoot, G., "Summary of the N1-P2 cortical auditory evoked potential to estimate the auditory threshold in adults". Seminars in hearing, 37(1), 1 (2016).

Virtanen, J., Ahveninen, J., Ilmoniemi, R. J., Naatanen, R., & Pekkonen, E., "Replicability of MEG and EEG measures of the auditory N1/N1m-response." Electroencephalography and Clinical Neurophysiology/Evoked Potentials Section, 108(3), 291-298(1998).

Gascoyne, L., Furiong, P. L., Hillebrand, A., Worthen, S. F., & Witton, C., "Localising the auditory N1m with event-related beamformers: localisation accuracy following bilateral and unilateral stimulation." Scientific reports, 6(1), 1-9 (2016).

(56) References Cited

OTHER PUBLICATIONS

Borna, A., Carter, T.R., Goldberg, J.D., Colombo, A.P., Jau, Y.Y., Berry, C., McKay, J., Stephen, J., Weisend, M. and Schwindt, P.D., "A 20-channel magnetoencephalography system based on optically pumped magnetometers." Physics in Medicine & Biology, 62(23), 8909 (2017).
Pyragius, T., Marin Florez, H., & Fernholz, T. (2019). A Voigt effect based 3D vector magnetometer. Physical Review A, 100(2), https://doi.org/10.1103/PhysRevA.100.023416.
Rui Zhang, Rahul Mhaskar, Ken Smith, Easswar Balasubramaniam, Mark Prouty. "All Optical Scalar Atomic Magnetometer Capable of Vector Measurement," Submitted on Nov. 17, 2020. https://arxiv.org/abs/2011.08943; Geometries, Inc., San Jose, CA, 95131, USA.
Arjen Stolk, Ana Todorovic, Jan-Mathijs Schoffelen, and Robert Oostenveld. "Online and offline tools for head movement compensation in MEG." Neuroimage 68 (2013): 39-48.
Bagherzadeh, Yasaman, Daniel Baldauf, Dimitrios Pantazis, and Robert Desimone. "Alpha synchrony and the neurofeedback control of spatial attention." Neuron 105, No. 3 (2020): 577-587.
Stephan Lau et al : "Optimal Magnetic Sensor Vests for Cardiac Source Imaging", SENSORS, vol. 16, No. 6, May 24, 2016 (May 24, 2016), p. 754.
Rodriguez Vince: "On the design of door-less access passages to shielded enclosures", 2017 Antenna Measurement Techniques Association Symposium (AMTA), AMTA, Oct. 15, 2017 (Oct. 15, 2017), pp. 1-6.
Orang Alem et al: "Fetal magnetocardiography measurements with an array of microfabricated optically pumped magnetometers", Physics in Medicine and Biology, Institute of Physics Publishing, Bristol GB, vol. 60, No. 12, Jun. 4, 2015 (Jun. 4, 2015), pp. 4797-4811.
Smit Mobile Equipment B.V.: "Mobile MRI", Dec. 19, 2016 (Dec. 19, 2016), Retrieved from the Internet: URL:https://web.archive.org/web/20161219022429/https://smit.one/products/mobile%20mri.html.
Zhang Xin et al: "Detection and analysis of MEG signals in occipital region with double-channel OPM sensors", Journal of Neuroscience Methods, Elsevier Science Publisher B. V., Amsterdam, NL, vol. 346, Sep. 17, 2020 (Sep. 17, 2020).
Hill RM, Boto E, Holmes N, et al. A tool for functional brain imaging with lifespan compliance [published correction appears in Nat Commun. Dec. 4, 2019;10(1):5628], NatCommun. 2019;10(1):4785. Published Nov. 5, 2019. doi:10.1038/S41467-019-12486-x.
Zetter, R., Iivanainen, J. & Parkkonen, L. Optical Co-registration of MRI and On-scalp MEG. Sci Rep 9, 5490 (2019). https://doi.org/10.1038/s41598-019-41763-4.
Garrido-Jurado, Sergio, Rafael Muñoz-Salinas, Francisco José Madrid-Cuevas and Manuel J. Marín-Jiménez. "Automatic generation and detection of highly reliable fiducial markers under occlusion." Pattern Recognit. 47 (2014):2280-2292.
Hill RM, Boto E, Rea M, et al. Multi-channel whole-head OPM-MEG: Helmet design and a comparison with a conventional system [published online ahead of print, May 29, 2020]. Neuroimage. 2020;219:116995. doi: 10.1016/j.neuroimage.2020.116995.
V. Kazemi and J. Sullivan, "One millisecond face alignment with an ensemble of regression trees," 2014 IEEE Conference on Computer Vision and Pattern Recognition, Columbus, OH, 2014, pp. 1867-1874, doi: 10.1109/CVPR.2014.241.
Holmes, N., Tierney, T.M., Leggett, J. et al. Balanced, bi-planar magnetic field and field gradient coils for field compensation in wearable magnetoencephalography. Sci Rep 9, 14196 (2019).
N. Holmes, J. Leggett, E. Boto, G. Roberts, R.M. Hill, T.M. Tierney, V. Shah, G.R. Barnes, M.J. Brookes, R. Bowtell A bi-planarcoil system for nulling background magnetic fields in scalp mounted magnetoencephalography Neuroimage, 181 (2018) pp. 760-774.
J. M. Leger et. al., In-flight performance of the Absolute Scalar Magnetometer vector mode on board the Swarm satellites, Earth, Planets, and Space (2015) 67:57.
Alexandrov, E. B., Balabas, M. V., Kulyasov, V. N., Ivanov, A. E., Pazgalev, A. S., Rasson, J. L., . . . (2004). Three-component variometer based on a scalar potassium sensor. Measurement Science and Technology, 15(5), 918-922.
Gravrand, O., Khokhlov, A., & JL, L. M. (2001). On the calibration of a vectorial 4He pumped magnetometer. Earth, planets and space , 53 (10), 949-958.
Borna, Amir & Carter, Tony & Colombo, Anthony & Jau, Y-Y & McKay, Jim & Weisend, Michael & Taulu, Samu & Stephen, Julia & Schwindt, Peter. (2018). Non-Invasive Functional-Brain-Imaging with a Novel Magnetoencephalography System. 9 Pages.
Vrba J, Robinson SE. Signal processing in magnetoencephalography. Methods. 2001;25(2):249-271. doi:10.1006/meth.2001.1238.
Uusitalo M and Ilmoniemi R., 1997, Signal-space projection method for separating MEG or EEG into components. Med. Biol. Comput. (35) 135-140.
Taulu S and Kajola M., 2005, Presentation of electromagnetic multichannel data: the signal space separation method. J. Appl. Phys. (97) 124905 (2005).
Taulu S, Simola J and Kajola M., 2005, Applications of the signal space separation method. IEEE Trans. Signal Process. (53) 3359-3372 (2005).
Taulu S, Simola J., 2006, Spatiotemporal signal space separation method for rejecting nearby interference in MEG measurements. Phys. Med. Biol. (51) 1759-1768 (2006).
Johnson, et al., Magnetoencephalography with a two-color pump-probe, fiber-coupled atomic magnetometer, Applied Physics Letters 97, 243703 2010.
Zhang, et al., Magnetoencephalography using a compact multichannel atomic magnetometer with pump-probe configuration, AIP Advances 8, 125028 (2018).
Xia, H. & Ben-Amar Baranga, Andrei & Hoffman, D. & Romalis, Michael. (2006). Magnetoencephalography with an atomic magnetometer. Applied Physics Letters—Appl Phys Lett. 89. 10.1063/1.2392722.
Ilmoniemi, R. (2009). The triangle phantom in magnetoencephalography. In 24th Annual Meeting of Japan Biomagnetism and Bioelecctromagnetics Society, Kanazawa, Japan, 28.29.5.2009 (pp. 6263).
Oyama D. Dry phantom for magnetoencephalography—Configuration, calibration, and contribution. J Neurosci Methods. 2015;251:24-36. doi: 0.1016/j.jneumeth.2015.05.004.
Chutani, R., Maurice, V., Passilly, N. et al. Laser light routing in an elongated micromachined vapor cell with diffraction gratings for atomic clock applications. Sci Rep 5, 14001 (2015). https://doi.org/10.1038/srep14001.
Eklund, E. Jesper, Andrei M. Shkel, Svenja Knappe, Elizabeth A. Donley and John Kitching. "Glass-blown spherical microcells for chip-scale atomic devices." (2008).
Jimenez-Martinez R, Kennedy DJ, Rosenbluh M, et al. Optical hyperpolarization and NMR detection of 129Xe on a microfluidic chip. Nat Commun. 2014;5:3908. Published May 20, 2014. doi:10.1038/ncomms4908.
Boto, Elena, Sofie S. Meyer, Vishal Shah, Orang Alem, Svenja Knappe, Peter Kruger, T. Mark Fromhold, et al. "A New Generation of Magnetoencephalography: Room Temperature Measurements Using Optically-Pumped Magnetometers." NeuroImage 149 (Apr. 1, 2017): 404-14.
Bruno, A. C., and P. Costa Ribeiro. "Spatial Fourier Calibration Method for Multichannel SQUID Magnetometers." Review of Scientific Instruments 62, No. 4 (Apr. 1, 1991): 1005-9.
Chella, Federico, Filippo Zappasodi, Laura Marzetti, Stefania Della Penna, and Vittorio Pizzella. "Calibration of a Multichannel MEG System Based on the Signal Space Separation Method." Physics in Medicine and Biology 57 (Jul. 13, 2012): 4855-70.
Pasquarelli, A, M De Melis, Laura Marzetti, Hans-Peter Muller, and S N Erné. "Calibration of a Vector-MEG Helmet System." Neurology & Clinical Neurophysiology□: NCN 2004 (Feb. 1, 2004): 94.
Pfeiffer, Christoph, Lau M. Andersen, Daniel Lundqvist, Matti Hämäläinen, Justin F. Schneiderman, and Robert Oostenveld. "Localizing On-Scalp MEG Sensors Using an Array of Magnetic Dipole Coils." PLOS ONE 13, No. 5 (May 10, 2018): e0191111.
Vivaldi, Valentina, Sara Sommariva, and Alberto Sorrentino. "A Simplex Method for the Calibration of a MEG Device." Communications in Applied and Industrial Mathematics 10 (Jan. 1, 2019): 35-46.

(56) References Cited

OTHER PUBLICATIONS

Nagel, S., & Spüler, M. (2019). Asynchronous non-invasive high-speed BCI speller with robust non-control state detection. Scientific Reports, 9(1), 8269.

Thielen, J., van den Broek, P., Farquhar, J., & Desain, P. (2015). Broad-Band Visually Evoked Potentials: Re(con) volution in Brain-Computer Interfacing. PloS One, 10(7), e0133797. https://doi.org/10.1371/journal.pone.0133797.

J. Kitching, "Chip-scale atomic devices," Appl. Phys. Rev. 5(3), 031302 (2018), 39 pages.

US 11,604,237 B2

DEVICES, SYSTEMS, AND METHODS WITH OPTICAL PUMPING MAGNETOMETERS FOR THREE-AXIS MAGNETIC FIELD SENSING

CROSS-REFERENCE TO RELATED APPLICATIONS

This application claims the benefit of U.S. Provisional Patent Application Ser. No. 63/135,364, filed Jan. 8, 2021, and U.S. Provisional Patent Application Ser. No. 63/158,700, filed Mar. 9, 2021, both of which are incorporated herein by reference in their entireties.

FIELD

The present disclosure is directed to the area of magnetic field measurement systems including systems for magnetoencephalography (MEG). The present disclosure is also directed to magnetic field measurement systems and methods for suppressing background or interfering magnetic fields.

BACKGROUND

In the nervous system, neurons propagate signals via action potentials. These are brief electric currents which flow down the length of a neuron causing chemical transmitters to be released at a synapse. The time-varying electrical currents within an ensemble of neurons generate a magnetic field. Magnetoencephalography (MEG), the measurement of magnetic fields generated by the brain, is one method for observing these neural signals.

Existing systems for observing or measuring MEG typically utilize superconducting quantum interference devices (SQUIDs) or collections of discrete optically pumped magnetometers (OPMs). SQUIDs require cryogenic cooling which is bulky and expensive and requires a lot of maintenance which preclude their use in mobile or wearable devices.

BRIEF SUMMARY

One embodiment is a magnetic field measurement system that includes a magnetometer having at least one vapor cell, at least one light source configured to direct at least two light beams through the at least one vapor cell, and at least one detector configured to receive the light beams directed through the at least one vapor cell, wherein at least two of the at least two light beams are not parallel and do not overlap; at least one magnetic field generator disposed adjacent the at least one vapor cell and configured to modify an external magnetic field experienced by the at least one vapor cell; and at least one processor coupled to the magnetometer and the at least one magnetic field generator. The at least one processor is configured for: applying a first modulation pattern, $b_{mod}(t)$, to the at least one magnetic field generator to modulate a magnetic field at the at least one vapor cell of the magnetometer using the first modulation pattern, wherein $b_{mod}(t)=[c_x \cos(\omega t)+s_x \sin(\omega t), c_y \cos(\omega t)+s_y \sin(\omega t), c_z \cos(\omega t)+s_z \sin(\omega t)]$, wherein $c_x$, $s_x$, $c_y$, $s_y$, $c_z$, and $s_z$ are amplitudes and $\omega$ is a frequency of the first modulation pattern, wherein at least one of each pair $(c_i, s_i)$ is non-zero, where i is x, y, or z; directing the at least one light source to direct the at least two light beams through the at least one vapor cell; receiving signals from the at least one detector in response to receiving the light beams during the application of the first modulation pattern; and determining three orthogonal components of the external magnetic field at the magnetometer using the received signals.

In at least some embodiments, $c_x$, $s_y$, and $c_z$ equal zero and $s_x$, $c_y$, and $s_z$ equal $B_m$, wherein $B_m$ is an amplitude of the first modulation pattern. In at least some embodiments, $c_x$, $s_y$, and $c_z$ equal $B_m$ and $s_x$, $c_y$, and $s_z$ equal zero, wherein $B_m$ is an amplitude of the first modulation pattern.

In at least some embodiments, the at least one vapor cell is only one vapor cell. In at least some embodiments, the at least one vapor cell is a plurality of vapor cells. In at least some embodiments, the at least two light beams include at least three light beams and at least two of the at least three light beams are parallel to each other. In at least some embodiments, the at least two of the at least two light beams that are not parallel are orthogonal to each other.

In at least some embodiments, determining the three orthogonal components of the external magnetic field includes determining a matrix M, wherein the external magnetic field is equal to M#S, wherein M# is a pseudo-inverse of the matrix M and S is the received signals. In at least some embodiments, $S=[S_1, S_2]$, wherein $$S_1 = A_{1c} \cos(\omega t) + A_{1s} \sin(\omega t)$$

and $$S_2 = A_{2c} \cos(\omega t) + A_{2s} \sin(\omega t).$$

In at least some embodiments, $$M = \begin{bmatrix} dA_{1c}/dB_x & dA_{1c}/dB_y & dA_{1c}/dB_z \\ dA_{1s}/dB_x & dA_{1s}/dB_y & dA_{1s}/dB_z \\ dA_{2c}/dB_x & dA_{2c}/dB_y & dA_{2c}/dB_z \\ dA_{2s}/dB_x & dA_{2s}/dB_y & dA_{2s}/dB_z \end{bmatrix}.$$

In at least some embodiments, M is determined from measurements. In at least some embodiments, M is determined using theory or numerical simulations.

In at least some embodiments, the at least one processor is further configured for applying a second modulation pattern, $b_{mod2}(t)$, to the at least one magnetic field generator to modulate a magnetic field at the at least one vapor cell of the magnetometer using the second modulation pattern, wherein $b_{mod2}(t)$ is identical to $b_{mod}(t)$ except that $b_{mod2}(t)$ is rotated 180 degrees about an axis relative to $b_{mod}(t)$; directing the at least one light source to direct the at least two light beams through the at least one vapor cell; and receiving signals from the at least one detector in response to receiving the light beams during the application of the second modulation pattern; wherein determining the three orthogonal components of the external magnetic field includes averaging the received signals during application of the first modulation pattern and the received signals during application of the second modulation pattern.

Another embodiment is a processor readable non-transitory storage media that includes instructions for determining three orthogonal components of an external magnetic field at a magnetometer, wherein execution of the instructions by one or more processors, performs actions, including applying a first modulation pattern, $b_{mod}(t)$, to at least one magnetic field generator disposed adjacent to at least one vapor cell of the magnetometer to modulate a magnetic field at the at least one vapor cell of the magnetometer using the first modulation pattern, wherein $b_{mod}(t)=[c_x \cos(\omega t)+s_x \sin(\omega t), c_y \cos(\omega t)+s_y \sin(\omega t), c_z \cos(\omega t)+s_z \sin(\omega t)]$, wherein $c_x$, $s_x$, $c_y$, $s_y$, $c_z$, and $s_z$ are amplitudes and $\omega$ is a frequency of the first modulation pattern, wherein at least one of each pair ($c_i$, $s_i$) is non-zero, where i is x, y, or z; directing the at least one light source to direct the at least two light beams through the at least one vapor cell; receiving signals from at least one detector of the magnetometer in response to receiving the light beams at the at least one detector during the application of the first modulation pattern; and determining the three orthogonal components of the external magnetic field at the magnetometer using the received signals.

A further embodiment is a magnetic field measurement system that includes a magnetometer having at least one vapor cell, at least one light source configured to direct at least one light beam through the at least one vapor cell, and at least one detector configured to receive the at least one light beam directed through the at least one vapor cell; at least one magnetic field generator disposed adjacent the at least one vapor cell and configured to modify an external magnetic field experienced by the at least one vapor cell; and at least one processor coupled to the magnetometer and the at least one magnetic field generator, wherein the at least one processor is configured for: applying a first modulation pattern, $b_{mod}(t)$, to the at least one magnetic field generator to modulate a magnetic field at the at least one vapor cell of the magnetometer using the first modulation pattern, wherein $b_{mod}(t)$ includes at least two modulation frequencies, wherein at least two of the modulation frequencies are not an integer multiple of the other of the at least two of the modulation frequencies; directing the at least one light source to direct the at least two light beams through the at least one vapor cell; receiving signals from the at least one detector in response to receiving the light beams during the application of the first modulation pattern; and determining three orthogonal components of the external magnetic field at the magnetometer using the received signals.

In at least some embodiments, $b_{mod}(t) = c_1 \cos(\omega_1 t) + s_1 \sin(\omega_1 t) + c_2 \cos(\omega_2 t) + s_2 \sin(\omega_2 t)$, wherein $c_1$, $s_1$, $c_2$, and $s_2$ are vectors and $\omega_1$ and $\omega_2$ are the at least two modulation frequencies.

In at least some embodiments, determining the three orthogonal components of the external magnetic field includes determining a matrix M, wherein the external magnetic field is equal to M#S, wherein M# is the pseudo-inverse of the matrix M and S is the received signals. In at least some embodiments, the at least one processor is further configured for determining $b_{mod}(t)$ by selecting a metric J that is a function of M or M#; determining values of J for different candidates for $b_{mod}(t)$; and, based on the values of J, selecting one of the candidates. In at least some embodiments, J is a norm of M. In at least some embodiments, selecting one of the candidates includes selecting the one of the candidates with a lowest value of J.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

Figure 1A:
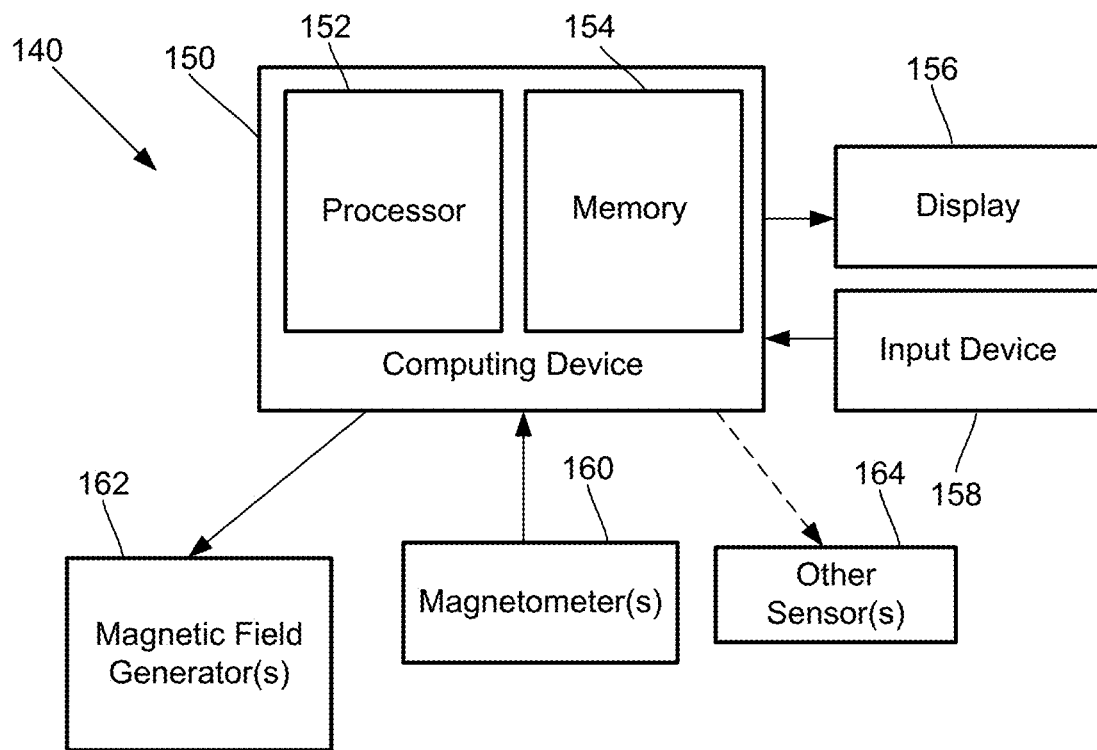
FIG. 1A is a schematic block diagram of one embodiment of a magnetic field measurement system, according to the invention.

The present disclosure is directed to the area of magnetic field measurement systems including systems for magnetoencephalography (MEG). The present disclosure is also directed to magnetic field measurement systems and methods for suppressing background or interfering magnetic fields. Although the present disclosure utilizes magnetoencephalography (MEG) to exemplify the OPMs, systems, and methods described herein, it will be understood that the OPMs, systems, and methods can be used in any other suitable application.

Herein the terms "ambient background magnetic field" and "background magnetic field" are interchangeable and used to identify the magnetic field or fields associated with sources other than the magnetic field measurement system and the magnetic field sources of interest, such as biological source(s) (for example, neural signals from a user's brain) or non-biological source(s) of interest. The terms can include, for example, the Earth's magnetic field, as well as magnetic fields from magnets, electromagnets, electrical devices, and other signal or field generators in the environment, except for the magnetic field generator(s) that are part of the magnetic field measurement system.

The terms "gas cell", "vapor cell", and "vapor gas cell" are used interchangeably herein. Below, a gas cell containing alkali metal vapor is described, but it will be recognized that other gas cells can contain different gases or vapors for operation.

An optically pumped magnetometer (OPM) is a basic component used in optical magnetometry to measure magnetic fields. While there are many types of OPMs, in general magnetometers operate in two modalities: vector mode and scalar mode. In vector mode, the OPM can measure one, two, or all three vector components of the magnetic field; while in scalar mode the OPM can measure the total magnitude of the magnetic field.

Vector mode magnetometers measure a specific component of the magnetic field, such as the radial and tangential components of magnetic fields with respect the scalp of the human head. Vector mode OPMs often operate at zero-field and may utilize a spin exchange relaxation free (SERF) mode to reach femto-Tesla sensitivities. A SERF mode OPM is one example of a vector mode OPM, but other vector mode OPMs can be used at higher magnetic fields. These SERF mode magnetometers can have high sensitivity but may not function in the presence of magnetic fields higher than the linewidth of the magnetic resonance of the atoms of about 10 nT, which is much smaller than the magnetic field strength generated by the Earth. As a result, conventional SERF mode magnetometers often operate inside magnetically shielded rooms that isolate the sensor from ambient magnetic fields including Earth's magnetic field.

Magnetometers operating in the scalar mode can measure the total magnitude of the magnetic field. (Magnetometers in the vector mode can also be used for magnitude measurements.) Scalar mode OPMs often have lower sensitivity than SERF mode OPMs and are capable of operating in higher magnetic field environments.

The magnetic field measurement systems described herein can be used to measure or observe electromagnetic signals generated by one or more magnetic field sources (for example, neural signals or other biological sources) of interest. The system can measure biologically generated magnetic fields and, at least in some embodiments, can measure biologically generated magnetic fields in an unshielded or partially shielded environment. Aspects of a magnetic field measurement system will be exemplified below using magnetic signals from the brain of a user; however, biological signals from other areas of the body, as well as non-biological signals, can be measured using the system. This technology can also be applicable for uses outside biomedical sensing. In at least some embodiments, the system can be a wearable MEG system that can be used outside a magnetically shielded room. Examples of wearable MEG systems are described in U.S. Patent Application Publication No. 2020/0057115 and U.S. Provisional Patent Application Ser. Nos. 63/031,469; 63/076,015; 63/037,407; and 63/058,616, all of which are incorporated herein by reference in their entireties.

A magnetic field measurement system can utilize one or more magnetic field sensors. Magnetometers will be used herein as an example of magnetic field sensors, but other magnetic field sensors may also be used. FIG. 1A is a block diagram of components of one embodiment of a magnetic field measurement system 140. The system 140 can include a computing device 150 or any other similar device that includes a processor 152, a memory 154, a display 156, an input device 158, one or more magnetometers 160 (for example, an array of magnetometers) which can be OPMs, one or more magnetic field generators 162, and, optionally, one or more other sensors 164 (e.g., non-magnetic field sensors). The system 140 and its use and operation will be described herein with respect to the measurement of neural signals arising from one or more magnetic field sources of interest in the brain of a user as an example. It will be understood, however, that the system can be adapted and used to measure signals from other magnetic field sources of interest including, but not limited to, other neural signals, other biological signals, as well as non-biological signals.

The computing device 150 can be a computer, tablet, mobile device, field programmable gate array (FPGA), microcontroller, or any other suitable device for processing information or instructions. The computing device 150 can be local to the user or can include components that are non-local to the user including one or both of the processor 152 or memory 154 (or portions thereof). For example, in at least some embodiments, the user may operate a terminal that is connected to a non-local computing device. In other embodiments, the memory 154 can be non-local to the user.

The computing device 150 can utilize any suitable processor 152 including one or more hardware processors that may be local to the user or non-local to the user or other components of the computing device.

Any suitable memory 154 can be used for the computing device 150. The memory 154 illustrates a type of computer-readable media, namely computer-readable storage media. Computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 156 can be any suitable display device, such as a monitor, screen, or the like, and can include a printer. In some embodiments, the display is optional. In some embodiments, the display 156 may be integrated into a single unit with the computing device 150, such as a tablet, smart phone, or smart watch. In at least some embodiments, the display is not local to the user. The input device 158 can be, for example, a keyboard, mouse, touch screen, track ball, joystick, voice recognition system, or any combination thereof, or the like. In at least some embodiments, the input device is not local to the user.

The magnetic field generator(s) 162 can be, for example, Helmholtz coils, solenoid coils, planar coils, saddle coils, electromagnets, permanent magnets, or any other suitable arrangement for generating a magnetic field. As an example, the magnetic field generator 162 can include three orthogonal sets of coils to generate magnetic fields along three orthogonal axes. Other coil arrangements can also be used. The optional sensor(s) 164 can include, but are not limited to, one or more position sensors, orientation sensors, accelerometers, image recorders, or the like or any combination thereof.

The one or more magnetometers 160 can be any suitable magnetometer including, but not limited to, any suitable optically pumped magnetometer. Arrays of magnetometers are described in more detail herein. In at least some embodiments, at least one of the one or more magnetometers (or all of the magnetometers) of the system is arranged for operation in the SERF mode. Examples of magnetic field measurement systems, such as MEG systems, or methods of making such systems or components for such systems are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; 2020/0341081; 2020/0381128; 2020/0400763; US 2021/0011094; 2021/0015385; 2021/0041512; and 2021/0041513; U.S. patent application Ser. Nos. 17/004,507; and 17/087,988, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/037,407; 63/052,327; 63/058,616; 63/076,015; 63/076,880; 63/080,248; 63/089,456; 63/135,364; 63/136,093; 63/136,415; and 63/140,150, all of which are incorporated herein by reference in their entireties. The OPMs, OPM modules, and other system components described in these references can be used in the MEG and other magnetic field measurement systems and methods described herein.

Figure 1B:
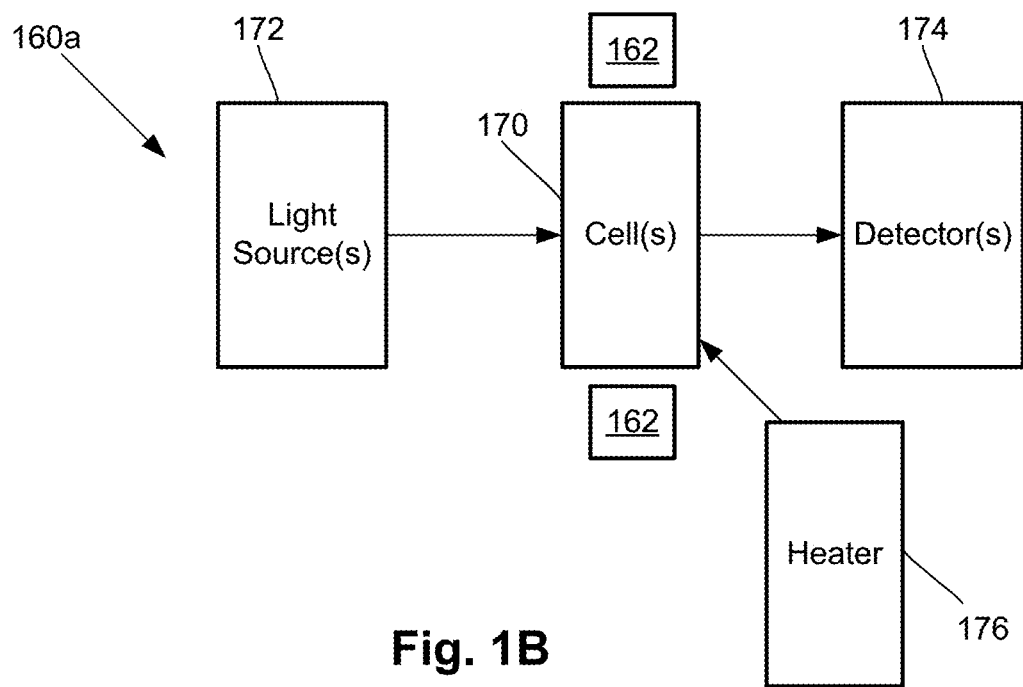
FIG. 1B is a schematic block diagram of one embodiment of a magnetometer, such as an OPM module, according to the invention.

FIG. 1B is a schematic block diagram of one embodiment of a magnetometer, such as an OPM module 160a, which includes one or more vapor cells 170 (also referred to as "cells") such as alkali metal vapor cells; a heating device 176 to heat the vapor cell(s) 170; one or more light sources 172 (which can include multiple different light sources, such as a pump light source and a probe light source); and one or more detectors 174. In addition, coils of a magnetic field generator 162 can be positioned around the vapor cell(s) 170. The vapor cell(s) 170 can include, for example, an alkali metal vapor (for example, rubidium in natural abundance, isotopically enriched rubidium, potassium, or cesium, or any other suitable alkali metal such as lithium, sodium, or francium) and, optionally, one, or both, of a quenching gas (for example, nitrogen) and a buffer gas (for example, nitrogen, helium, neon, or argon). In some embodiments, the vapor cell may include the alkali metal atoms in a prevaporized form prior to heating to generate the vapor.

The light source(s) 172 can each include, for example, a laser to, respectively, optically pump the alkali metal atoms and probe the vapor cell. The light source(s) 172 may also include optics (such as lenses, waveplates, collimators, polarizers, and objects with reflective surfaces) for beam shaping and polarization control and for directing the light from the light source to the cell and detector. Examples of suitable light sources include, but are not limited to, a diode laser (such as a vertical-cavity surface-emitting laser (VCSEL), distributed Bragg reflector laser (DBR), distributed feedback laser (DFB)), external cavity diode laser (ECDL), light-emitting diode (LED), lamp, or any other suitable light source. In at least some embodiments, light can be delivered to the vapor cell via free-space optics or through fiber optic cables.

The detector(s) 174 can include, for example, an optical detector to measure the optical properties of the transmitted probe light field amplitude, phase, or polarization, as quantified through optical absorption and dispersion curves, spectrum, or polarization or the like or any combination thereof. Examples of suitable detectors include, but are not limited to, a photodiode, charge coupled device (CCD) array, CMOS array, camera, photodiode array, single photon avalanche diode (SPAD) array, avalanche photodiode (APD) array, or any other suitable optical sensor array that can measure the change in transmitted light at the optical wavelengths of interest.

Figure 2:
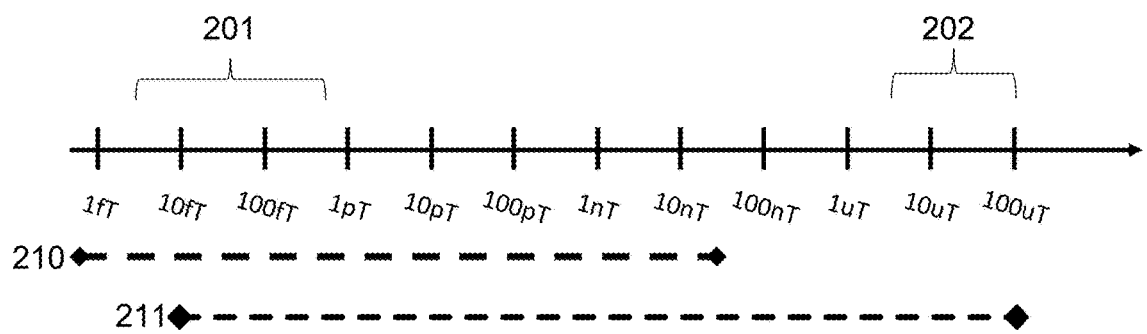
FIG. 2 shows a magnetic spectrum with lines indicating dynamic ranges of magnetometers operating in different modes.

FIG. 2 shows the magnetic spectrum from 1 fT to 100 μT in magnetic field strength on a logarithmic scale. The magnitude of magnetic fields generated by the human brain are indicated by range 201 and the magnitude of the background ambient magnetic field, including the Earth's magnetic field, by range 202. The strength of the Earth's magnetic field covers a range as it depends on the position on the Earth as well as the materials of the surrounding environment where the magnetic field is measured. Range 210 indicates the approximate measurement range of a magnetometer (e.g., an OPM) operating in the SERF mode (e.g., a SERF magnetometer) and range 211 indicates the approximate measurement range of a magnetometer operating in a scalar mode (e.g., a scalar magnetometer.) Typically, a SERF magnetometer is more sensitive than a scalar magnetometer, but many conventional SERF magnetometers typically only operate up to about 0 to 200 nT while the scalar magnetometer starts in the 10 to 100 fT range but extends above 10 to 100 μT.

Many conventional magnetoencephalography (MEG) systems based on OPMs are sensitive to magnetic fields in one or two directions. Such systems may constrain the ability to perform source localization and may compromise the ability of the OPMs to operate in a dynamic environment where background magnetic fields can point in any direction. In contrast, as described herein, devices, systems, and methods can provide information about all three magnetic field components without significantly compromising magnetic field sensitivity, which may enhance source localization and the ability to operate in dynamically changing magnetic fields.

Examples of magnetic field measurement systems in which the embodiments described herein can be incorporated, and which present features that can be incorporated in the embodiments presented herein, are described in U.S. Patent Application Publications Nos. 2020/0072916; 2020/0056263; 2020/0025844; 2020/0057116; 2019/0391213; 2020/0088811; 2020/0057115; 2020/0109481; 2020/0123416; 2020/0191883; 2020/0241094; 2020/0256929; 2020/0309873; 2020/0334559; and 2020/0341081; U.S. patent application Ser. Nos. 16/884,672; 16/904,281; 16/922,898; 16/928,810; 16/984,720; 16/984,752; and Ser. No. 17/004,507, and U.S. Provisional Patent Application Ser. Nos. 62/689,696; 62/699,596; 62/719,471; 62/719,475; 62/719,928; 62/723,933; 62/732,327; 62/732,791; 62/741,777; 62/743,343; 62/747,924; 62/745,144; 62/752,067; 62/776,895; 62/781,418; 62/796,958; 62/798,209; 62/798,330; 62/804,539; 62/826,045; 62/827,390; 62/836,421; 62/837,574; 62/837,587; 62/842,818; 62/855,820; 62/858,636; 62/860,001; 62/865,049; 62/873,694; 62/874,887; 62/883,399; 62/883,406; 62/888,858; 62/895,197; 62/896,929; 62/898,461; 62/910,248; 62/913,000; 62/926,032; 62/926,043; 62/933,085; 62/960,548; 62/971,132; 62/983,406; 63/031,469; 63/037,407; 63/052,327; 63/058,616; 63/076,015; 63/076,880; 63/080,248; and 63/089,456, all of which are incorporated herein by reference in their entireties.

In at least some conventional arrangements, SERF OPMs include a single laser beam and magnetic field generator(s)

that produce either a linear or rotating magnetic field modulation. For example, the magnetic field modulation may be a rotating field as presented in the following equation:

$$b_{mod}(t)=[b_x(t),b_y(t),b_z(t)]=[B_m\cos(\omega t),B_m\sin(\omega t),0]$$

where $B_m$ is the amplitude of the applied modulation (for example, $B_m$ can be in the range of 50-150 nT), $\omega$ is the frequency of the modulation (for example, $\omega$=2 kHz), and x, y, z are the cardinal directions (for example, with coordinates chosen so that z is along the direction of the optical pumping laser.) This modulation $b_{mod}(t)$ has one modulation frequency ($\omega$) and is planar (i.e., the modulation is only in the xy plane with the z component being zero). For such a magnetic field modulation, if the alkali vapor cell is subjected to an additional small external magnetic field $B_{ext}$= $[B_y, B_y, B_z]$ (for example, a magnetic field arising from the brain or heart of a subject), the transmitted light is modulated according to the following:

$$S=A_c\cos(\omega t)+A_s\sin(\omega t).$$

The amplitudes $A_c$ and $A_s$, which can be measured via lock-in detection, are approximately linear in $B_x$ and $B_y$ and are relatively insensitive to $B_z$. This permits the determination of two orthogonal components of the external magnetic field.

In contrast to conventional modulation, which typically only provides for measurement of fields in two axes, other devices, systems, and methods can utilize modulation that facilitates measuring all three orthogonal components of a magnetic field. In at least some embodiments, access to all three magnetic field components can provide improvements to the localization of sources within the brain. In at least some embodiments, access to all three magnetic field components can provide improvements to noise rejection due to motion in external fields or due to perturbations such as moving vehicles, office furniture, or the like.

An oscillatory magnetic field is applied to an OPM module and then the light from the laser beam transmitted through regions of the vapor cell(s) of the OPM module is measured. The measurement of the light produces electrical signals from the detector(s). In at least some embodiments, the measurement the electrical signals can include lock-in demodulation. Application of the pseudo-inverse of the response matrix M to the electrical signals gives the value of the external magnetic field for all three spatial directions. This procedure can be extended to larger numbers of beams with spatial arrangements that give sensitivity to higher order magnetic field spatial gradients.

In at least some embodiments, the devices, systems, and methods include the modulation of two or more light beams to measure all three orthogonal components of a magnetic field. The light beams can be, for example, laser beams which will be used herein as an example, but it will be understood that any other suitable light beam can be used. At least two of the light beams are non-overlapping and non-parallel (for example, the two light beams are orthogonal to each other.) The light beams are directed through one or more vapor cells of a magnetometer while a modulated magnetic field is applied to the vapor cell(s).

Figure 3A:
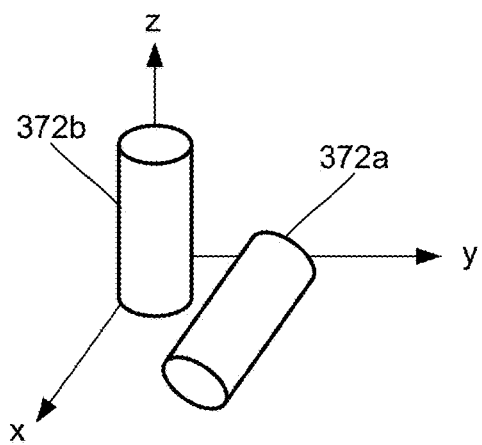
FIG. 3A shows a schematic illustration of two non-parallel, non-overlapping laser beams for directing at a vapor cell, according to the invention.

Devices, systems, and methods are disclosed herein that include OPM modules that contain a single vapor cell or two or more vapor cells. In at least some embodiments, to measure all three orthogonal components of a magnetic field two non-overlapping laser beams can be directed at one or more vapor cells. One example of such an arrangement of laser beams is illustrated in FIG. 3A where two laser beams 372a, 372b propagate in orthogonal directions and are non-overlapping. Each laser beam passes through a vapor cell 170 (FIG. 1B) and the transmitted beam is detected by detector(s) 174 (FIG. 1B), such as a photodiode. The laser beams 372a, 372b may pass through the same or different vapor cells, but are spatially separate from each other (for example, the separation (e.g., center-to-center) distance is greater than half the combined beamwidths of the two laser beams.)

In FIG. 3A, laser beam 372a propagates in the x direction and laser beam 372b propagates in the z direction. The laser wavelength is selected to excite the alkali metal atoms in the vapor cell. In at least some embodiments, the lasers are tuned to the D1 transition of an alkali atom (for example, the transition between the $^2S_{1/2}$ (ground state) and $^2P_{1/2}$ (excited state) at 795 nm for Rb) and laser beams are circularly polarized. As a non-limiting example, in at least some embodiments, the beam diameter is approximately 2 mm and the beams have about 200-1000 microWatts of power.

Figure 3B:
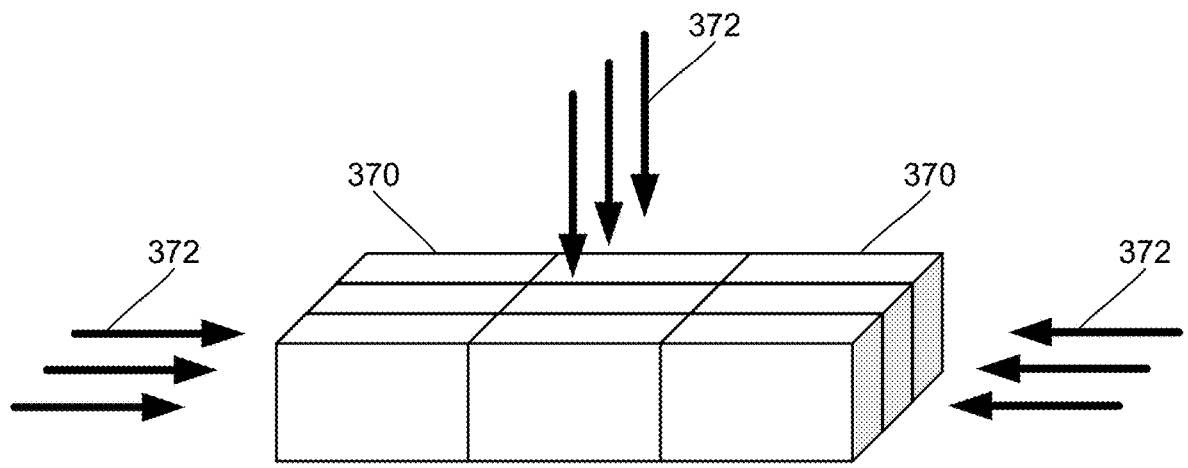
FIG. 3B is a schematic perspective view of nine vapor cells with laser beams directed at each vapor cell from one of three different directions, according to the invention.

FIG. 3B illustrates another arrangement with a 3×3 grid of vapor cells 370 and corresponding laser beams 372 (represented by arrows.) In this embodiment, one laser beam 372 is directed at each vapor cell 370. The laser beams 372 are distributed among three different directions—-z direction, +y direction, and -y direction (using the same coordinate system as FIG. 3A.) Again, the laser beams 372 do not overlap (for example, each laser beam is reflected back through the corresponding vapor cell to be received by a detector.)

In the devices, systems, and methods, a magnetic field modulation can be applied to the vapor cell(s) 370 of the OPM module(s) 160a (FIG. 1B) using the magnetic field generator(s) 162 (FIG. 1A). In at least some embodiments, the modulation pattern is selected to enable three-axis sensing of an external magnetic field. For example, the applied modulation pattern to the vapor cell(s) 370 of the OPM module(s) 160a (FIG. 1B) can be oscillatory (e.g., periodic) with one or more modulation frequencies. Each of these frequencies can have a selected three-dimensional spatial orientation. For example, the modulation may be a single-frequency cosine/sine modulation as described in Equation 1:

$$b_{mod}(t)=[b_x(t),b_y(t),b_z(t)] \qquad (1)$$
$$=[c_x\cos(\omega t)+s_x\sin(\omega t),c_y\cos(\omega t)+s_y\sin(\omega t),$$
$$c_z\cos(\omega t)+s_z\sin(\omega t)]$$

where $c_x$, $s_x$, $c_y$, $s_y$, $c_z$, and $s_z$ are six parameters that set the x, y, z components for the cosine and sine terms in the corresponding spatial direction and. For example, the six parameters may be chosen as $(c_x, c_y, s_y; c_z, s_y)$=(0, $B_m$; $B_m$, 0; 0, $B_m$) which results in the modulation pattern of Equation 2:

$$b_{mod}(t)=[B_m\sin(\omega t),B_m\cos(\omega t),B_m\sin(\omega t)] \qquad (2)$$

which has a cosine oscillation imposed along the x and z axes, and a sine oscillation imposed along the y axis, and where $B_m$ is the size of the imposed modulation (for example, $B_m$ may be a value in the range of 0.1 and 500 nanoTesla). It will be recognized that $(c_x, s_x; c_y, s_y; c_z, s_y)$=($B_m$, 0; 0, $B_m$; $B_m$, 0) can be used as well. These modulation patterns enable three-axis magnetic field measurement, as further described below. Other modulation patterns can be used and examples of additional modulation patterns that enable three-axis magnetic field measurements are presented below.

The modulation pattern can be introduced by an arrangement of coils, such as the magnetic field generator(s) 162 of FIG. 1A, surrounding or adjacent to the vapor cell(s) 370 of the OPM module(s) 160a (FIG. 1B). Hence the total magnetic field experienced by regions of vapor cell(s) 370 in the OPM module(s) 160a (FIG. 1B) is given by the sum of the external field plus the imposed modulation as described in Equation 3:

$$B_{total} = B_{ext} + b_{mod}(t) = [B_x + b_x(t), B_y + b_y(t), B_z + b_z(t)] \quad (3)$$

where $B_{ext} = (B_x, B_y, B_z)$ is the external field to be measured; $B_x$, $B_y$, and $B_z$ represent the external field's three spatial components to be measured; and $b_{mod}(t) = (b_x(t), b_y(t), b_z(t))$ represent the applied modulation pattern (for example, the modulation patterns of Equation 1 or Equation 2.) As an example, using the modulation pattern of Equation 2, the total magnetic field in the module can be represented by Equation 4:

$$B_{total} = [B_x + B_m \cos(\omega t), B_y + B_m \sin(\omega t), B_z + B_m \cos(\omega t)] \quad (4)$$

In at least some embodiments, the modulation frequency ω can be relatively large compared to the temporally varying components of the external magnetic field and thus the fast time dependence (t) has been stated explicitly in Equations 1 to 4 for purposes of clarity.

Through optical pumping and precession of the spins of the alkali metal atoms in the vapor cell(s) 170 in the external and modulated magnetic fields, the spin-polarization of the alkali metal atoms is modulated at the frequency ω by the modulation pattern. The spins of the alkali metal atoms modulate the intensity of the transmitted laser beams 372 at the same frequency. The transmitted laser beam 372 is converted to electrical signals by the detector(s) 174 (FIG. 1B). For the two non-overlapping laser beams 372a, 372b of FIG. 3A, the resulting signal $S(S_1, S_2)$ from the photodiode detector has components described by Equations 5a and 5b:

$$S_1 = A_{1c} \cos(\omega t) + A_{1s} \sin(\omega t) \quad (5a)$$

and $$S_2 = A_{2c} \cos(\omega t) + A_{2s} \sin(\omega t) \quad (5b)$$

In at least some embodiments, detector signals can be digitized and processed using, for example, digital signal processing (DSP) techniques on, for example, a field programmable array (FPGA) to extract signal amplitudes $A_{jc}$ and $A_{js}$ in real time or otherwise. For the modulation pattern of Equation 2, the amplitudes $A_{1c}$ and $A_{1s}$ are approximately linear in $B_z$ and $B_y$, respectively, for small $B_z$ and $B_y$. Similarly, the amplitudes $A_{2c}$ and $A_{2s}$ are approximately linear in $B_x$ and $B_y$, respectively. In at least some embodiments, these amplitudes are extracted from raw detector signals via lock-in demodulation and taken together can be used to form a measurement of all three magnetic field components.

In at least some embodiments, imperfections in coil geometry and phase shifts due to atoms and digital electronics, as well as other effects, can lead to mixing of the response between various demodulated quadratures and field axes. In at least some embodiments, this mixing can be removed using the pseudo-inversion of the response matrix $M = dS/dB_{ext}$ of Equation 6 (for S of Equations 5a and 5b):

$$M = \begin{bmatrix} dA_{1c}/dB_x & dA_{1c}/dB_y & dA_{1c}/dB_z \\ dA_{1s}/dB_x & dA_{1s}/dB_y & dA_{1s}/dB_z \\ dA_{2c}/dB_x & dA_{2c}/dB_y & dA_{2c}/dB_z \\ dA_{2s}/dB_x & dA_{2s}/dB_y & dA_{2s}/dB_z \end{bmatrix} \quad (6)$$

In at least some embodiments, the matrix M can be obtained from experiments (e.g., measurements), theory, or numerical simulations or from any combination thereof. In at least some embodiments, analysis of the detector signals can be performed to extract the matrix elements of M, which can then be used to demix the raw demodulator outputs, so that magnetic fields in orthogonal directions appear at the output of the device in only a single channel.

Estimates of the three magnetic field components can then be obtained as $B_{est} = M^\# S$ where $M^\#$ is the pseudo-inverse of the matrix M and S is the column vector formed from the measured detector signal amplitudes:

$$S = \begin{bmatrix} A_{1c} \\ A_{1s} \\ A_{2c} \\ A_{2s} \end{bmatrix}$$

Figure 4:
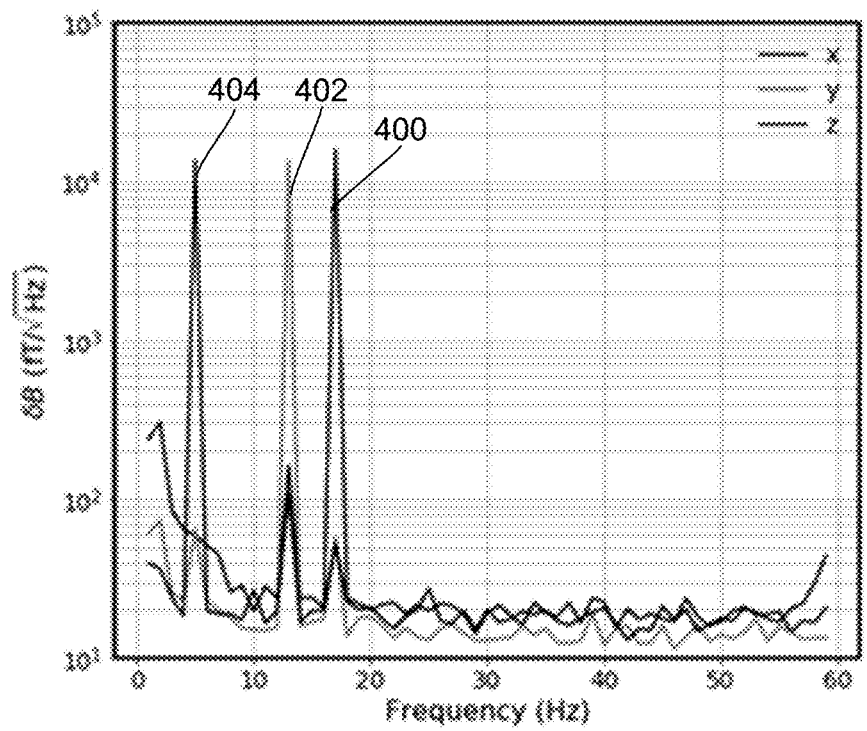
FIG. 4 is a graph of the experimental three-axis noise spectra (x-spectra 400, y-spectra 402, z-spectra 404) obtained using an OPM module traversed by nine laser beams in total, according to the invention.

As an example, FIG. 4 below is a graph of the experimental three-axis noise spectra (x-spectra 400, y-spectra 402, z-spectra 404) obtained using an OPM module traversed by nine laser beams in total, such as the arrangement in FIG. 3B: three beams propagating in the −z direction, three beams propagating in the +x direction, and three beams propagating in the −x direction. A single-frequency modulation with to $\omega = 2\pi \times 1$ kHz is applied, according to Equation 2, with a modulation amplitude $B_m = 42$ nT. The three-axis vector field information was obtained by demixing 2×9 lock-in quadratures with an 18×3 response matrix M. Calibration tones of approximately 20 pT peak amplitude were applied at 17 Hz, 13 Hz, and 5 Hz in the x, y, and z directions, respectively. Cross talk between axes is at the level of 1 part in 100, as indicated by the amplitude of the small peaks with respect to the nominal peak. The noise floor above 20 Hz was below 20 fT/Hz$^{1/2}$.

Figure 5:
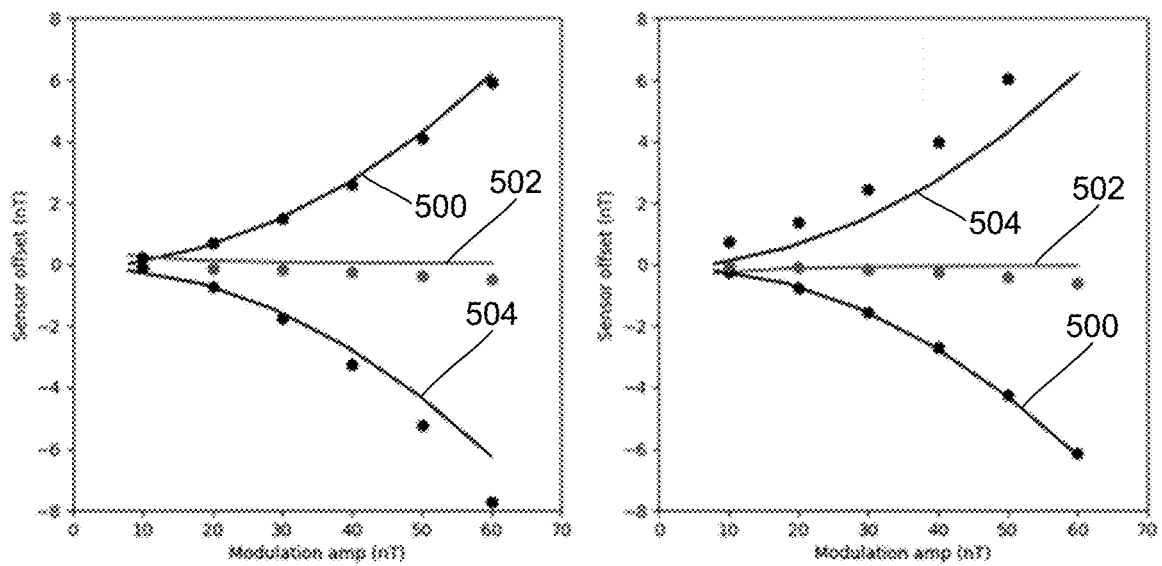
FIG. 5 illustrates graphs of offsets for two modulation patterns that differ only by rotation around the y-axis by 180 degrees, according to the invention.

The addition of modulation in a third magnetic field direction may introduce offsets in the measurements. These modulation-induced offsets cam be distinguished from actual magnetic field measurements. In at least some embodiments, changing the phase of the modulation pattern along one axis (for example, the y axis) by 180 degrees reverses the sign of the modulation induced offsets, as illustrated in FIG. 5 by changing the phase of the y-axis modulation. FIG. 5 illustrates the x-offsets 500, y-offsets 502, and z-offsets 504. Averaging measurements of signals with modulation about the selected action with the nominal phase and with a 180-degree phase shift can be used to eliminate or reduce the modulation-induced offset. In FIG. 5, the left panel presents the offsets induced by modulation in three axes for the modulation pattern presented in Eq. 4 (solid line is numerical simulation, points are experimental measurements), as a function of the modulation amplitude. The right panel shows the offsets if the phase of the y-axis modulation is shifted by 180 degrees.

In at least some embodiments, this second modulation pattern, $b_{mod2}(t)$, is identical to $b_{mod}(t)$ except that $b_{mod2}(t)$ is rotated 180 degrees about an axis relative to $b_{mod}(t)$. It will be recognized that the selection of the y-axis is merely an example and that the elimination of the offsets can be performed along any axis that is not an axis of transmission of the two non-overlapping laser beams. In at least some embodiments, the axis of rotation is orthogonal to the two axes of transmission of the two non-overlapping laser beams.

In at least some embodiments, the methods, devices, and systems include measuring all three orthogonal components of a magnetic field using only a single laser beam traversing a single vapor cell, or a single region of a vapor cell, of an OPM module. In these embodiments, one or more regions of the vapor cell can be used to measure all three components of a magnetic field by selecting imposed oscillatory modulation patterns, such as patterns with two or more modulation frequencies, and demodulating the light output from each vapor cell or vapor cell region at two or more frequencies (for example, at one or more of the primary frequencies or one or more harmonic or beat frequencies or any combination thereof.)

As a non-limiting example, the modulation b(t) is given by Equation 7:

$$b_{mod}(t) = c_1 \cos(\omega_1 t) + s_1 \sin(\omega_1 t) + c_2 \cos(\omega_2 t) + s_2 \sin(\omega_2 t) \quad (7)$$

where $c_1$, $s_1$, $c_2$, and $s_2$ are vectors, $\omega_1$ is a first modulation frequency, and $\omega_2$ is a second modulation frequency. Such a modulation pattern exploits the nonlinear dynamics of optically pumped alkali metal atoms (as for example described by the Bloch equations), and also exploits the interaction of the two frequencies that give rise to beat and harmonic frequencies whose size and phase can provide information regarding the external magnetic field $B_{ext}$. Such a modulation pattern can, for example, allow measurement of all three components of the external magnetic field using a single vapor cell, or single region of a vapor cell, with just one laser beam through it, to allow.

Other modulation patterns can utilize three or more frequencies. Moreover, the shape of the modulation can have shapes different from a sine or cosine shape, including, but not limited to, triangular or square waves, forward or backward ramps, or other shapes that are, for example, achievable by Fourier terms, e.g., $f(t) = a_1 \cos(\omega t + p_1) + a_2 \cos(2\omega t + p_2) + \ldots a_N \cos(N\omega t + p_N)$ where $a_1, a_2, \ldots, a_N$ and $p_1, p_2, \ldots, p_N$ are coefficients defining the shape f(t). In at least some embodiments, the shape f(t) can replace $\cos(\omega t)$ or $\sin(\omega t)$ terms in any modulation pattern and $\omega$ can be replaced by $\omega_1$, $\omega_2$, or any other number of frequencies.

A modulation sequence $b_{mod}(t)$ can be selected to maximize or increase a performance metric, such as signal-to-noise (SNR) ratio, bandwidth, spatial resolution, or the like or any combination thereof. Modulation sequences can utilize one or more of the following features: two, three, four or more frequencies; more complex wave patterns, such as triangular, square, and more generally shaped waves rather than just sinusoidal waves; or amplitude vectors (for example, $c_1$, $s_1$, $c_2$, $s_2$, $c_3$, $s_3$, ... ) that parameterize the modulation pattern.

Figure 6:
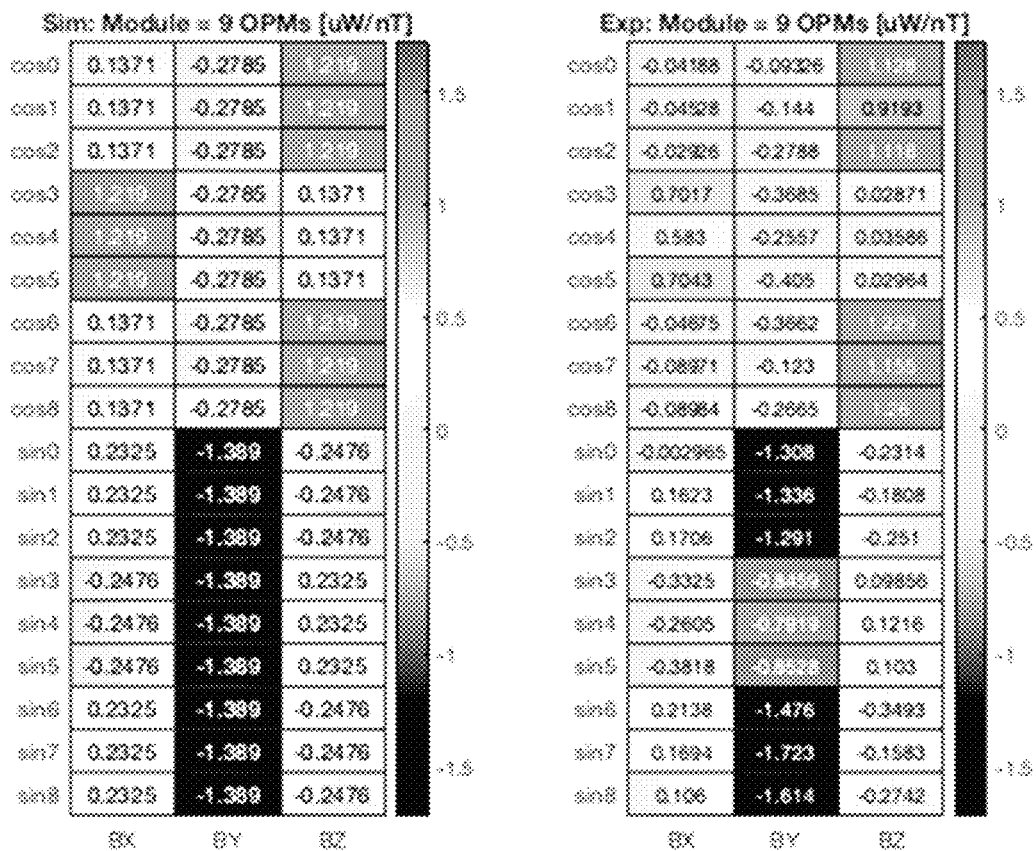
FIG. 6 illustrates two response matrices M, the left matrix was determined by measurements and the right matrix was determined by simulations, according to the invention.

As previously described, M is the matrix that maps from the external magnetic field $B_{ext} = [B_x, B_y, B_z]$ to the change in the quadrature coefficients, as presented in Equation 6. Specifically, each element of M is the rate-of-change of that quadrature coefficient $A_i$ with respect to $B_j$. For example, $dA_{1c}/dB_x$ is the rate of change of the $A_{1c}$ coefficient of Equation 5a with respect to $B_x$. The M matrix depends on the modulation sequence, and can be determined by experiment, simulation, or any combination thereof. FIG. 6 illustrates two examples of an M matrix for three magnetic field components ($B_x$, $B_y$, $B_z$-columns) versus resulting changes in sine and cosine demodulations for nine vapor cells of one OPM module, such as the arrangement in FIG. 3B. This is for an example modulation sequence of $b_{mod}(t) = 70$ nT[sin($\omega t$), cos($\omega t$), sin($\omega t$)] where $\omega$ is 1 kHz. In FIG. 6 the left M matrix was determined by simulation and the right M matrix was determined for the same case from experimental data (right matrix). Comparison exhibits reasonable agreement between the two matrices. Small differences between the two matrices may be related to small differences in experimental parameters.

In the situation where there is more than one demodulation frequency, for example, a two-frequency modulation and demodulation at primary frequencies ($\omega_1$, $\omega_2$), harmonic frequencies ($2\omega_1$, $2\omega_2$), and beat frequencies ($\omega_1 - \omega_2$, $\omega_1 + \omega_2$, $2\omega_1 - \omega_2$, $2\omega_1 + \omega_2$, ... ), the matrix M will have additional rows corresponding to additional demodulation frequencies.

S=[M] $B_{ext}$ (except for noise and experimental error), where S is the column vector formed from the measured demodulated signal amplitudes and $B_{ext} = [B_x, B_y, B_z]$ is the external magnetic field. The matrix M depends on the modulation pattern $b_{mod}(t)$. If, as in Equation 7, the modulation sequence $b_{mod}(t)$ is parameterized by the parameter vectors $c_1$, $s_1$, $c_2$, $s_2$, then M is a function of these vectors leading to Equation 8:

$$S = [M] B_{ext} = [M(b_{mod})] B_{ext} = [M(c_1, s_1, c_2, s_2)] B_{ext}. \quad (8)$$

A different M matrix arises for different choices of the $c_1$, $s_1$, $c_2$, $s_2$ vectors. It may be desirable to find the parameters $c_1$, $s_1$, $c_2$, $s_2$ that yield an M matrix that enables or enhances three-axis sensing of the external magnetic field. A metric can be defined that reflects the quality of the choice of the M matrix (or equivalently the choice of $c_1$, $s_1$, $c_2$, $s_2$.) An example, metric J is the norm of the pseudo-inverse of $M(c_1, s_1, c_2, s_2)$ where $J = \|M^\#(c_1, s_1, c_2, s_2)\|$ where $\|X\|$ denotes the norm of a matrix X, and $M^\#$ is the pseudo-inverse of M. This metric J depends on the parameterization $c_1$, $s_1$, $c_2$, $s_2$ of the modulation pattern $b_{mod}(t)$. The norm $\|X\|$ can be the matrix 2-norm, the matrix infinity norm, or any other suitable matrix norm. Different selected norms will produce different metrics.

Above is one appropriate choice of a metric J that facilitates selection of a modulation parameterization $c_1$, $s_1$, $c_2$, $s_2$ that will maximize or improve the signal-to-noise ratio (SNR) ratio for three-axis sensing by a single vapor cell, or a single region of a vapor cell, with a single laser beam. Experimental noise d will be present in the column vector S of measured demodulation signal amplitudes. With this noise taken into account, S=[M] $B_{ext}$+d. In this case, with noise included, Equation 8 becomes Equation 9:

$$B_{est} = [M^\#] S = [M^\#]([M] B_{ext} + d) \quad (9)$$

where $B_{est}$ is the inferred estimate of the external magnetic field $B_{ext}$. The pseudo-inverse $M^\#$ inverts out the matrix M, thus Equation 9 becomes Equation 10:

$$B_{est} = B_{ext} + [M^\#] d \quad (10)$$

The estimate of magnetic field in Equation 10 has two contributions, one corresponding to the external field $B_{ext}$ and one corresponding to the contribution from noise. To maximize or increase the SNR, the term $[M^\#] d$ can be made small, for any noise d. This can be achieved by reducing or minimizing the norm of $M^\#$ or, in other words, reducing or minimizing the selected metric $J = \|M^\#(c_1, s_1, c_2, s_2)\|$. Doing so will reduce or minimize the effect of noise, thus increasing or maximizing the SNR. In a special case when M is not pseudo-invertible, or is almost not pseudo invertible (i.e., when the selected modulation parameters are so poor that no real information can be gained on the external magnetic field), J will be infinite or very large. Thus, reducing or minimizing J with respect to $c_1$, $s_1$, $c_2$, $s_2$ will select a modulation parameterization where $\|M^\#(c_1, s_1, c_2, s_2)\|$ is relatively small. In such instances, not only can information be gained for all the axes of the external magnetic field $B_{ext}=[B_x, B_y, B_z]$ but also the SNR will be maximized or increased.

Other metrics J can also be used. For example, the norm of the matrix M can be maximized or increased, instead of minimizing or reducing the norm of its pseudo-inverse $M^\#$. Other metrics J may also be used, including weighted norms, or maximizing/increasing or minimizing/decreasing specific elements or features of M or $M^\#$.

As an example, in the case of three-axis sensing via a single vapor cell, or a single region of a vapor cell, with one laser beam, for each selection of $c_1$, $s_1$, $c_2$, $s_2$, the matrix M can be obtained via simulation or experiments. For example, the matrix M can be obtained using simulations using the Bloch equations for polarization as a function of modulation pattern; simulations using the Bloch equations with additional coupled sets of equations for light propagation; or simulations using other physical/mathematical representations of vapor cells at either lower or higher mathematical/physical complexity. As other examples, M may be attained by semi-analytic approximation methods for various mathematical/physical models or M may be attained experimentally for different choices of modulation pattern $b_{mod}(t)$. Any of these methods can be combined, such as, for example, allowing partial semi-analytical or numerical assessment and partial experimental assessment of M. M may be determined for different cases of the modulation patterns $b_{mod}(t)$ or for different cases of the parameters that parameterize the modulation (e.g., for different cases of $c_1$, $s_1$, $c_2$, $s_2$). For each case, once M is known its pseudo-inverse M# and any performance metric (e.g., norms of either matrix, weighted norms, or other combinations of matrix coefficients) can be calculated. The performance metric(s) can be used to select a modulation pattern or modulation parameters.

In at least some embodiments, investigation of a parameter space can be performed using any suitable method including, but not limited to, a random scattershot approach or selecting parameters from a random distribution. The metric(s) J can be calculated for the sets of parameters and one of the sets of parameters can be selected. In at least some embodiments, investigation of the parameter space can be performed more systematically using, for example, gradient-free optimization search algorithms, such as a pattern search. In at least some embodiments, a gradient-free optimization search searches further in the direction of already found acceptable parameters and searches less in the direction of unacceptable parameters. In at least some embodiments, gradient-based search methods can be used in which analysis is carried out to compute the gradient of J with respect to the parameters. In at least some embodiments, this can be conducted numerically or semi-analytically. Other methods of searching can include, for example, genetic algorithms, neural networks, swarms, and other method for optimization of nonlinear problems.

In at least some embodiments, the M matrix is extended to capture the mapping from external magnetic field $B_{ext}$ to demodulation coefficients for multiple vapor cell regions and two or more laser beams. For example, M can reflect the mapping from the external magnetic field to the change in demodulation amplitude coefficients for any number of vapor cell regions. This M can be for one demodulation frequency or for more than one demodulation frequency. M can be for a modulation at one frequency or modulation at 2 or more frequencies. Elements of M can be weighted equally for all vapor cell regions or some elements of M can be weighted higher or lower to focus the on selected vapor cell region(s) in the OPM module.

In at least some embodiments, the magnetic field measurements can be used directly in open loop mode or in a feedback loop to extend dynamic range. The three-axis magnetic sensing methods described herein can be used, for example, to directly detect neural activity by placing the sensor adjacent to the skull. For applications involving source localization of neural activity, measurements of three vector components may enable more accurate source reconstruction than measurements of only one or two vector components. An OPM module may also be used as a reference sensor to help remove common mode noise associated with drifting external fields or to remove noise associated with user motion in a background field or to aid in magnetic-based localization methods, for example, to find the location of a sensor with respect to a fixed calibration source.

Applications for three-axis sensing outside of the space of MEG are numerous, including, but not limited to, magnetic anomaly detection, geophysical and space exploration, and navigation.

Figure 7:
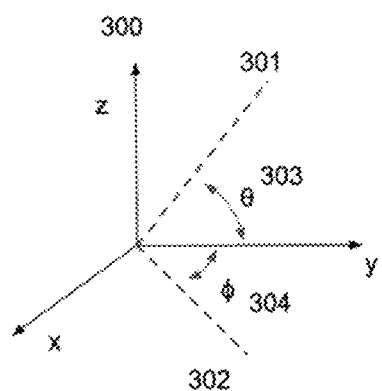
FIG. 7 illustrates an implementation of an adaptive single-axis sensor, according to the invention.

In at least some embodiments, control of modulation fields in three axes can facilitate sensing directions for magnetometers configured to sense one or two magnetic field components. As an example, magnetic fields of neural origin may generate a linearly polarized magnetic field in an arbitrary direction. If that magnetic field direction is known, the SNR can be increased by tuning the sensing axis to increase sensitivity to magnetic fields in a particular direction. FIG. 7 illustrates an implementation of an adaptive single-axis sensor (such as an OPM). A three-dimensional coordinate frame 300 is presented for the three-axis sensor. Magnetic field components along x and y in the X-Y plane and along z and y in the Z-Y plane are measured indirectly by introducing oscillatory fields, such as those described in Equation 1.

In the adaptive single-axis sensor the modulating fields are configured such that $$b_{\_ac}=[b_{x\_ac}\cos(\omega t), b_{y\_ac}\cos(\omega t), b_{z\_ac}\cos(\omega t)]$$

The magnetometer is thus most sensitive to field components parallel to the dashed line 301, where $\theta=\operatorname{atan}(b_{z\_ac}/b_{y\_ac})$ 303 and $\varphi=\operatorname{atan}(b_{x\_ac}, b_{y\_ac})$ 304. Thus, by tailoring these ratios magnetic fields can be sampled at selected directions using single-axis sensing. Increasing the sensitivity to magnetic fields in two directions can be achieved similarly by adjusting the modulation fields so that the plane of the rotating field corresponds to the desired direction of the external magnetic field that is to be sensed.

In at least some embodiments, the devices, systems, and methods described herein can provide three-axis sensing with sensitivity. In at least some embodiments, the devices, systems, and methods described herein can provide simple absorption-based measurements operating at zero field. In at least some embodiments, the devices, systems, and methods described herein can provide arrangements where multiple laser beams illuminate different regions of space enabling gradiometry or improved magnetic field measurement via averaging.

In at least some embodiments, the devices, systems, and methods described herein can provide improved signal-to-noise (SNR) ratio, improved bandwidth (can measure faster signals), improved spatial resolution, or improved ability to extract information (e.g., all three components of a magnetic field, instead of just two), or any combination thereof.

Figure 8:
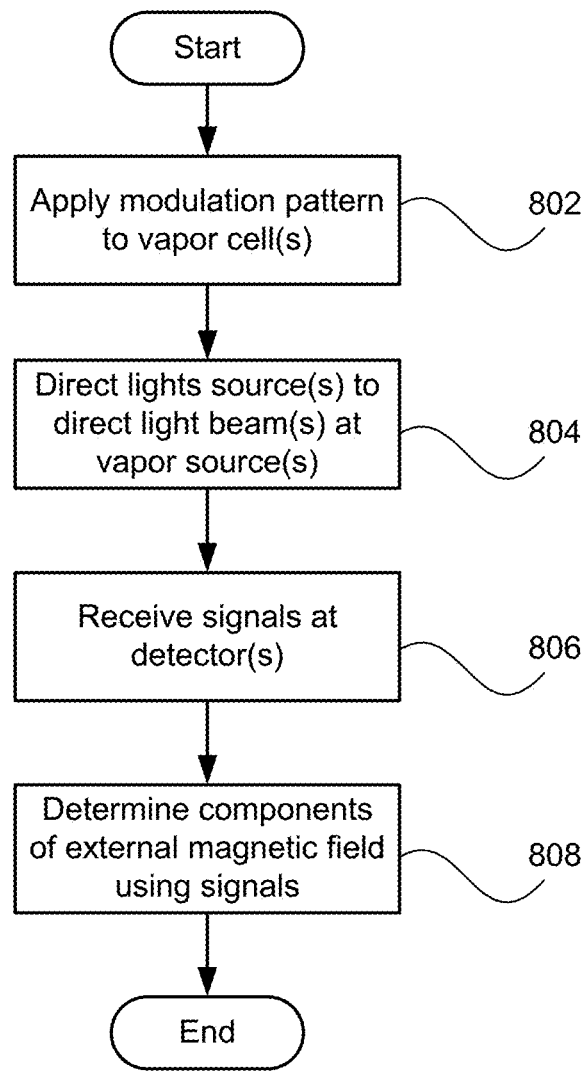
FIG. 8 is a flowchart of one method of determining three orthogonal components of an external magnetic field at a magnetometer, according to the invention.

FIG. 8 illustrates a method for determining three orthogonal components of an external magnetic field at a magnetometer. In step 802, a modulation pattern, $b_{mod}(t)$, is applied to magnetic field generator(s) to modulate a magnetic field at one or more vapor cell(s) of a magnetometer using the modulation pattern. In at least some embodiments, the modulation pattern is applied along three orthogonal axes or is applied using multiple frequencies. Examples of modulation fields include, but are not limited to, a) $b_{mod}(t)=[c_x \cos(\omega t)+s_x \sin(\omega t), c_y \cos(\omega t)+s_y \sin(\omega t), c_z \cos(\omega t)+s_z \sin(\omega t)]$, where $c_x$, $s_x$, $c_y$, $s_y$, $c_z$, and $s_z$ are amplitudes and $\omega$ is a frequency of the modulation pattern, where at least one of each pair $(c_i, s_i)$ is non-zero, where i is x, y, or z (Equation 2 is one example of this modulation pattern) orb) $b_{mod}(t)=c_1 \cos(\omega_1 t)+s_1 \sin(\omega_1 t)+c_2 \cos(\omega_2 t)+s_2 \sin(\omega_2 t)$, where $c_1$, $s_1$, $c_2$, and $s_2$ are vectors, $\omega_1$ is a first modulation frequency, and $\omega_2$ is a second modulation frequency.

In step 804, at least one light source is directed to direct the at least one light beam or at least two light beams through the at least one vapor cell. For example, for the modulation pattern a) in the preceding paragraph, at least two light beams are directed to at least one vapor cell with at least two of the at least two light beams being not parallel and not overlapping. Such arrangements are illustrated in FIGS. 3A and 3B. As another example, for the modulation pattern b) in the preceding paragraph, at least one light beam is direction to at least one vapor cell.

In step 806, signals from at least one detector are received in response to the light beams being received by the at least one detector after transmission through the at least one vapor cell. The signals are modulated by the modulation pattern due the alkali metal atoms in the vapor cell and are also representative of the external magnetic field.

In step 808; the three orthogonal components of the external magnetic field at the magnetometer are determined using the received signals as described above. The determination may include using the matrix M described above. The determination may also include addressing offsets caused by modulation along the third orthogonal axis by repeating steps 802 to 806 using another modulation pattern, $b_{mod2}(t)$, that is identical to $b_{mod}(t)$ except that $b_{mod2}(t)$ is rotated 180 degrees about an axis relative to $b_{mod}(t)$.

The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification provides a description of the invention and its manufacture and use. Since many embodiments of the invention can be made without departing from the spirit and scope of the invention, the invention also resides in the claims hereinafter appended.

What is claimed as new and desired to be protected by Letters Patent of the United States is:

1. A magnetic field measurement system, comprising:
   a magnetometer comprising at least one vapor cell, at least one light source configured to direct at least two light beams through the at least one vapor cell, and at least one detector configured to receive the at least two light beams directed through the at least one vapor cell, wherein at least two of the at least two light beams are not parallel and do not overlap;
   at least one magnetic field generator disposed adjacent the at least one vapor cell and configured to modify an external magnetic field experienced by the at least one vapor cell; and
   at least one processor coupled to the magnetometer and the at least one magnetic field generator, wherein the at least one processor is configured for:
   applying a first modulation pattern, $b_{mod}(t)$, to the at least one magnetic field generator to modulate a magnetic field at the at least one vapor cell of the magnetometer using the first modulation pattern, wherein $b_{mod}(t)=[c_x \cos(\omega t)+s_x \sin(\omega t), c_y \cos(\omega t)+s_y \sin(\omega t), c_z \cos(\omega t)+s_z \sin(\omega t)]$, wherein $c_x$, $s_x$, $c_y$, $s_y$, $c_z$, and $s_z$ are amplitudes and $\omega$ is a frequency of the first modulation pattern, wherein at least one of each pair $(c_i, s_i)$ is non-zero, where i is x, y, or z;
   directing the at least one light source to direct the at least two light beams through the at least one vapor cell;
   receiving signals from the at least one detector in response to receiving the at least two light beams during the application of the first modulation pattern; and
   determining three orthogonal components of the external magnetic field at the magnetometer using the received signals.

2. The magnetic field measurement system of claim 1, wherein $c_x$, $s_y$, and $c_z$ equal zero and $s_x$, $c_y$, and $s_z$ equal $B_m$, wherein $B_m$ is an amplitude of the first modulation pattern.

3. The magnetic field measurement system of claim 1, wherein $c_x$, $s_y$, and $c_z$ equal $B_m$ and $s_x$, $c_y$, and $s_z$ equal zero, wherein $B_m$ is an amplitude of the first modulation pattern.

4. The magnetic field measurement system of claim 1, wherein the at least one vapor cell is only one vapor cell.

5. The magnetic field measurement system of claim 1, wherein the at least one vapor cell is a plurality of vapor cells.

6. The magnetic field measurement system of claim 1, wherein the at least two light beams comprise at least three light beams and at least two of the at least three light beams are parallel to each other.

7. The magnetic field measurement system of claim 1, wherein the at least two of the at least two light beams that are not parallel are orthogonal to each other.

8. The magnetic field measurement system of claim 1, wherein determining the three orthogonal components of the external magnetic field comprises determining a matrix M, wherein the external magnetic field is equal to M#S, wherein M# is a pseudo-inverse of the matrix M and S is the received signals.

9. The magnetic field measurement system of claim 8, wherein S=[$S_1$, $S_2$], wherein $$S_1 = A_{1c} \cos(\omega t) + A_{1s} \sin(\omega t)$$

and $$S_2 = A_{2c} \cos(\omega t) + A_{2s} \sin(\omega t).$$

10. The magnetic field measurement system of claim 9, wherein $$M = \begin{bmatrix} dA_{1c}/dB_x & dA_{1c}/dB_y & dA_{1c}/dB_z \\ dA_{1s}/dB_x & dA_{1s}/dB_y & dA_{1s}/dB_z \\ dA_{2c}/dB_x & dA_{2c}/dB_y & dA_{2c}/dB_z \\ dA_{2s}/dB_x & dA_{2s}/dB_y & dA_{2s}/dB_z \end{bmatrix}.$$

11. The magnetic field measurement system of claim 8, wherein M is determined from measurements.

12. The magnetic field measurement system of claim 8, wherein M is determined using a theory or numerical simulations.

13. The magnetic field measurement system of claim 1, wherein the at least one processor is further configured for:
applying a second modulation pattern, $b_{mod2}(t)$, to the at least one magnetic field generator to modulate a magnetic field at the at least one vapor cell of the magnetometer using the second modulation pattern, wherein $b_{mod2}(t)$ is identical to $b_{mod}(t)$ except that $b_{mod2}(t)$ is rotated 180 degrees about an axis relative to $b_{mod}(t)$;
directing the at least one light source to direct the at least two light beams through the at least one vapor cell; and
receiving signals from at least one detector in response to receiving the at least two light beams during the application of the second modulation pattern;
wherein determining the three orthogonal components of the external magnetic field comprises averaging the received signals during application of the first modulation pattern and the received signals during application of the second modulation pattern.

14. A processor readable non-transitory storage media that includes instructions for determining three orthogonal components of an external magnetic field at a magnetometer, wherein execution of the instructions by one or more processors, performs actions, comprising:
applying a first modulation pattern, $b_{mod}(t)$, to at least one magnetic field generator disposed adjacent to at least one vapor cell of the magnetometer to modulate a magnetic field at the at least one vapor cell of the magnetometer using the first modulation pattern, wherein $b_{mod}(t) = [c_x \cos(\omega t) + s_x \sin(\omega t), c_y \cos(\omega t) + s_y \sin(\omega t), c_z \cos(\omega t) + s_z \sin(\omega t)]$, wherein $c_x$, $s_x$, $c_y$, $s_y$, $c_z$, and $s_z$ are amplitudes and $\omega$ is a frequency of the first modulation pattern;
directing the at least one light source to direct the at least two light beams through the at least one vapor cell;
receiving signals from at least one detector of the magnetometer in response to receiving the at least two light beams at the at least one detector during the application of the first modulation pattern; and
determining the three orthogonal components of the external magnetic field at the magnetometer using the received signals.

15. A magnetic field measurement system, comprising:
a magnetometer comprising at least one vapor cell, at least one light source configured to direct at least one light beam through the at least one vapor cell, and at least one detector configured to receive the at least one light beam directed through the at least one vapor cell;
at least one magnetic field generator disposed adjacent the at least one vapor cell and configured to modify an external magnetic field experienced by the at least one vapor cell; and
at least one processor coupled to the magnetometer and the at least one magnetic field generator, wherein the at least one processor is configured for:
applying a first modulation pattern, $b_{mod}(t)$, to the at least one magnetic field generator to modulate a magnetic field at the at least one vapor cell of the magnetometer using the first modulation pattern, wherein $b_{mod}(t)$ comprises at least two modulation frequencies, wherein at least two of the modulation frequencies are not an integer multiple of the other of the at least two of the modulation frequencies;
directing the at least one light source to direct the at least one light beam through the at least one vapor cell;
receiving signals from the at least one detector in response to receiving the at least one light beam during the application of the first modulation pattern; and
determining three orthogonal components of the external magnetic field at the magnetometer using the received signals.

16. The magnetic field measurement system of claim 15, wherein $b_{mod}(t) = c_1 \cos(\omega_1 t) + s_1 \sin(\omega_1 t) + c_2 \cos(\omega_2 t) + s_2 \sin(\omega_2 t)$, wherein $c_1$, $s_1$, $c_2$, and $s_2$ are vectors and $\omega_1$ and $\omega_2$ are the at least two modulation frequencies.

17. The magnetic field measurement system of claim 15, wherein determining the three orthogonal components of the external magnetic field comprises determining a matrix M, wherein the external magnetic field is equal to M#S, wherein M# is the pseudo-inverse of the matrix M and S is the received signals.

18. The magnetic field measurement system of claim 17, wherein the at least one processor is further configured for determining $b_{mod}(t)$ by selecting a metric J that is a function of M or M#; determining values of J for different candidates for $b_{mod}(t)$; and, based on the values of J, selecting one of the candidates.

19. The magnetic field measurement system of claim 18, wherein J is a norm of M.

20. The magnetic field measurement system of claim 19, wherein selecting one of the candidates comprises selecting the one of the candidates with a lowest value of J.

* * * * *